(12) United States Patent
Zhao et al.

(10) Patent No.: US 7,592,163 B2
(45) Date of Patent: Sep. 22, 2009

(54) **HIGHLY ACTIVE XYLOSE REDUCTASE FROM *NEUROSPORA CRASSA***

(75) Inventors: Huimin Zhao, Champaign, IL (US); Ryan Woodyer, Champaign, IL (US); Michael Simurdiak, Urbana, IL (US); Wilfred A. van der Donk, Champaign, IL (US)

(73) Assignees: The Board of Trustees of the University of Illinois, Urbana, IL (US); Biotechnology Research and Development Corporation, Peoria, IL (US)

( * ) Notice: Subject to any disclaimer, the term of this patent is extended or adjusted under 35 U.S.C. 154(b) by 0 days.

(21) Appl. No.: 12/123,279

(22) Filed: May 19, 2008

(65) Prior Publication Data

US 2008/0241900 A1    Oct. 2, 2008

Related U.S. Application Data

(62) Division of application No. 11/151,762, filed on Jun. 14, 2005, now Pat. No. 7,381,553.

(60) Provisional application No. 60/579,710, filed on Jun. 15, 2004.

(51) Int. Cl.
    *C12P 19/02*     (2006.01)
    *C12N 9/02*      (2006.01)
(52) U.S. Cl. ........................ 435/105; 435/189
(58) Field of Classification Search ........................ None
    See application file for complete search history.

(56) References Cited

U.S. PATENT DOCUMENTS 6,582,944 B1    6/2003    Hallborn et al.

OTHER PUBLICATIONS

Database EMBL-EBI (2000): "*Aspergillus niger* D-xylose reductase (xyrA) gene, complete cds," Accession No. AF219625.
Database UniProt (2004): "Hypothetical protein (Xylose reductase)," Accession No. Q7SD67.
Haldimann et al., "Conditional-replications, integration, excision, and retrieval plasmid-host systems for gene structure-function sutides of bacteria," *J. Bacteriol.*, 183 (21): 6384-6893 (2001).
Hasper et al., "The *Aspergillus niger* transcriptional activator XlnR, which is involved in the degradation of the polysaccharides xylan and cellulose, also regulates D-xylose reductase gene expression," *Molecular Microbiology*, 36 (1): 193-200 (2000).
Ikemi et al., "Sorbitol Production in Charged Membrane Bioreactor with Coenzyme Regeneration System: I. Selective Retainment of NADP(H) in a Continuous Reaction," *Biotechnology and Bioengineering*, 36: 149-154 (1990).
Jin et al., "Molecular cloning of XYL3 (D-xylulokinase) from *Pichia stipitis* and characterization of its physiological function," *Appl. Environ. Microbiol.*, 68 (3): 1232-1239 (2002).
Kavanagh et al., "Structure of xylose reductase bound to NAD+ and the basis for single and dual co-substrate specificity in family 2 aldo-keto reductases," *Biochem J.*, 373 (Pt 2): 319-326 (2003).
Kozma et al., "The crystal structure of rat liver AKR7A1. A dimeric member of the aldo-keto reductase superfamily," *J. Biol. Chem.*, 277 (18): 16285-16293 (2002).
Nidetzky et al., "Continuous Enzymatic Production of Xylitol with Simultaneous Coenzyme Regneration in a Charged Membrane Reactor," *Biotechnology and Bioengineering*, 52: 387-396 (1996).
Neuhauser et al., "NAD(P)H-dependent aldose reductase from the xylose-assimilating yeast *Candida tenius*. Isolation, characterization and biochemical properties of the enzyme," *Biochem. J.*, 326 (Pt 3): 683-692 (1997).
Rawat et al., "D-xylose catabolizing enzymes in *Neurospora crassa* and their relationship to D-xylose fermentation," *Biotechnology Letters*, 15 (11): 1173-1178 (1993).
Rawat et al., "Purification, kinetic characterization and involvement of tryptophan residue at the NADPH binding site of xylose reductase from *Neurospora crassa*," *Biochimica et Biophysica Acta*, 1293: 222-230 (1996).
Rawat et al., "Conformation and microenvironment of the active site of xylose redutase inferred by fluorescent chemoaffinity labeling," *Eur. J. Biochem.*, 243: 344-349 (1997).
Rawat et al., "Site and Significance of Cysteine Residues in Xylose Reductase from *Neurospora crassa* as Deduced by Fluorescence Studies," *Biochemical and Biophysical Research Communication*, 239 (3): 789-793 (1997).
Woodyer et al., "Heterologous Expression, Purification, and Characterization of a Highly Active Xylose Reductase from *Neurospora crassa*," *Applied and Environmental Microbiology*, 71 (3): 1642-1647 (2005).
Zhao et al., "The Production and Properties of a New Xylose Reductase from Fungus," *Applied Biochemistry and Biotechnology*, 70-72: 405-414 (1998).
International Search Report issued in PCT/US2005/020719 (2006).

*Primary Examiner*—Andrew Wang
*Assistant Examiner*—MD. Younus Meah
(74) *Attorney, Agent, or Firm*—Barnes & Thornburg LLP; Alice O. Martin

(57)    ABSTRACT

A new xylose reductase encoding gene from *Neurspora crassa* was heterologously expressed in *E. coli* as a His-tag fusion protein and subsequently purified in high yield. This xylose reductase was shown to have a high turnover rate and catalytic efficiency, high stability at room temperature, broad pH profile, and a preference of NADPH over NADH. This enzyme is utilized in production of xylitol and other sugar alcohols such as sorbitol and also in the metabolic enhancement of organisms used for fermentation of plant biomass into ethanol.

7 Claims, 9 Drawing Sheets

```
N. crassa        -----MVPAIKLNSGFDMPQVGFGLWKVDGSIASDVVYNAIKAGYRLFDGACDYGNEVEC
C. tenuis        MSAS--IPDIKLSSGHLMPSIGFGCWKLANATAGEQVYQAIKAGYRLFDGAEDYGNEKEV
C. tropicalis    MSTTPTIPTIKLNSGYEMPLVGFGCWKVNNETAADQIYNAIKTGYRLFDGAEDYGNEKEV
C. parapsilosis  MSTATASPAVKLNSGYEIPLVGFGCWKLTNDVASDQIYRAIKSGYRLFDGAEDYANEQEV
A. niger         ----MASPTVKLNSGYDMPLVGFGLWKVNNDTCADQIYHAIKEGYRLFDGACDYGNEVEA
                      *:**.**. :* :*** **:. ..: ;*.*** ******* **.** *

N. crassa        GQGVARAIKEGIVKREELFIVSKLWNTFHDGDRVEPIVRKQLADWGLEYFDLYLIDFPVA
C. tenuis        GDGVKRAIDEGLVKREEIFLTSKLWNNYHDPKNVETALNKILADLKVDYVDLFLIDFPIA
C. tropicalis    GEGINRAIKEGLVKREELFITSKLWNNFHDPKNVETAINKILSDLNIDYVDLFLIDFPIA
C. parapsilosis  GEGIKRAIKEGIVKREELFITSKLWNSFHDKKNVEVALYKILSDLNIDYVDLFYIDFPIA
A. niger         GQGIARAIKDGLVKREELFIVSKLWNSFHDGDRVEPICRKQLADWGIDYFDLYIVDFPIS
                  *:*: ***.:* :*****:*:.***** ..** *  *:* ::*.**: :****::

N. crassa        LEYVDPSVRYPPGWHFDGKSEIRPSKATIQETWTAMESLVEKGLSKSIGVSNFQAQLIYD
C. tenuis        FKFVPIEEKYPPGFYCGDGNKFVYEDVPILETWKALEKLVAAGKIKSIGVSNFPGALLID
C. tropicalis    FKFVPIEEKYPPGFYCGDGDKFHYEDVPLLDTWKALEKLVEAGKIKSIGISNFIGALIYD
C. parapsilosis  QKPVPIEKKYPPGFYCGDGDKWSIEEVPLLDTWRALEKLVDQGLAKSIGISNFSAQLIYD
A. niger         LKYVDPAVRYPPGWKSE-KDELEFGNATIQETWTAMESLVDKKLARSIGISNFSAQLVMD
                  : *   :***:; . .:   ...: ;** *:*.**   :***:*** . *: *

N. crassa        LLRYAKVRPATLQIEHHPYLVQQNLLNLAKAEGIAVIAYSSFGPASFREFNMEHAQKLQP
C. tenuis        LLRGAIIKPAVLQVEHHPYLQQPKLIEFAQKAGVTIIAYSSFGPQSFVEMNQGRALNIPT
C. tropicalis    LTRGATIKPAVLQIEHHPYLQQPKLIEYVQKAGIAITGYSSFGPQSFLPLESKRALNIPT
C. parapsilosis  LTRGCTIKPVALQIEHHPYLTQPKLVEYVQLHDIQITGYSSFGPQSFLEMDLKRALDIPV
A. niger         LLRYARIRPATLQIEHHPYLTQTRLVEYAQKEGLTVTAYSSFGPLSFLELSVQKAVDSPP
                 *:*  . ::*.:**:****** *  .*::  .:  . :*.***** ** *:. .*  .

N. crassa        LLEDPTIKAIGDKYNKDPAQVLLRWATQRGLATIPKSSREATMKSNLNSLDFDLSEEDIK
C. tenuis        LFAHDTIKAIAAKYNKTPAEVLLRWAAQRGIAVIPKSNLPERLVQNRSFNTFDLIKEDFE
C. tropicalis    LFEHETIKSIADKHGKSPAQVLLRWATQRNIAVIPKSNNPERLAQNLSVVDFDLIKDDLD
C. parapsilosis  LLEEPTVKSIADKHGKSPAQVLLRYQTQRGIAVIPKSNSPDRMAQNLSVIDPELTQDDLQ
A. niger         LFEHQLVKSIAEKHGRTPAQVLLRWATQRGIAVIPKSNPQRLKQNLDVTGWNLEEEEIK
                 *:.  .  :*:*.  *::  **:****:*.   ;**:*:*.*.    . * .  ::*  ::;;.

N. crassa        TISGFDRGIRFNQPTNYFSAENLWIFG
C. tenuis        EIAKLDIGLRFNIPWDWDNIP-IFV--
C. tropicalis    NIAKLDIGLRFNIPWDWDNIP-IFV--
C. parapsilosis  AIAELDCNLRFNEPWDFSNIP-VFV--
A. niger         AISGLDRGLRFNEPLGYGLYAPIF---
                  *: :* .:***:*  .:       ::
```

FIG. 1

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 322
<212> TYPE: PRT
<213> ORGANISM: Neurospora crassa

<400> SEQUENCE: 2

Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
                20                  25                  30

Tyr Asn Ala Ile Lys Ala Gly Tyr Arg Leu Phe Asp Gly Ala Cys Asp
            35                  40                  45

Tyr Gly Asn Glu Val Glu Cys Gly Gln Gly Val Ala Arg Ala Ile Lys
        50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Leu Tyr Leu Ile His Phe
            100                 105                 110

Pro Val Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220

Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
                245                 250                 255
```

```
Leu Leu Arg Trp Ala Thr Gln Arg Gly Leu Ala Ile Ile Pro Lys Ser
            260                 265                 270

Ser Arg Glu Ala Thr Met Lys Ser Asn Leu Asn Ser Leu Asp Phe Asp
        275                 280                 285

Leu Ser Glu Glu Asp Ile Lys Thr Ile Ser Gly Phe Asp Arg Gly Ile
    290                 295                 300

Arg Phe Asn Gln Pro Thr Asn Tyr Phe Ser Ala Glu Asn Leu Trp Ile
305                 310                 315                 320

Phe Gly

<210> SEQ ID NO 3
<211> LENGTH: 322
<212> TYPE: PRT
<213> ORGANISM: Candida tenuis

<400> SEQUENCE: 3

Met Ser Ala Ser Ile Pro Asp Ile Lys Leu Ser Ser Gly His Leu Met
1               5                   10                  15

Pro Ser Ile Gly Phe Gly Cys Trp Lys Leu Ala Asn Ala Thr Ala Gly
            20                  25                  30

Glu Gln Val Tyr Gln Ala Ile Lys Ala Gly Tyr Arg Leu Phe Asp Gly
        35                  40                  45

Ala Glu Asp Tyr Gly Asn Glu Lys Glu Val Gly Asp Gly Val Lys Arg
    50                  55                  60

Ala Ile Asp Glu Gly Leu Val Lys Arg Glu Glu Ile Phe Leu Thr Ser
65                  70                  75                  80

Lys Leu Trp Asn Asn Tyr His Asp Pro Lys Asn Val Glu Thr Ala Leu
                85                  90                  95

Asn Lys Thr Leu Ala Asp Leu Lys Val Asp Tyr Val Asp Leu Phe Leu
            100                 105                 110

Ile His Phe Pro Ile Ala Phe Lys Phe Val Pro Ile Glu Glu Lys Tyr
        115                 120                 125

Pro Pro Gly Phe Tyr Cys Gly Asp Gly Asn Asn Phe Val Tyr Glu Asp
    130                 135                 140

Val Pro Ile Leu Glu Thr Trp Lys Ala Leu Glu Lys Leu Val Ala Ala
145                 150                 155                 160

Gly Lys Ile Lys Ser Ile Gly Val Ser Asn Phe Pro Gly Ala Leu Leu
                165                 170                 175

Leu Asp Leu Leu Arg Gly Ala Thr Ile Lys Pro Ala Val Leu Gln Val
            180                 185                 190

Glu His His Pro Tyr Leu Gln Gln Pro Lys Leu Ile Glu Phe Ala Gln
        195                 200                 205

Lys Ala Gly Val Thr Ile Thr Ala Tyr Ser Ser Phe Gly Pro Gln Ser
    210                 215                 220

Phe Val Glu Met Asn Gln Gly Arg Ala Leu Asn Thr Pro Thr Leu Phe
225                 230                 235                 240

Ala His Asp Thr Ile Lys Ala Ile Ala Ala Lys Tyr Asn Lys Thr Pro
                245                 250                 255

Ala Glu Val Leu Leu Arg Trp Ala Ala Gln Arg Gly Ile Ala Val Ile
            260                 265                 270

Pro Lys Ser Asn Leu Pro Glu Arg Leu Val Gln Asn Arg Ser Phe Asn
        275                 280                 285

Thr Phe Asp Leu Thr Lys Glu Asp Phe Glu Glu Ile Ala Lys Leu Asp
    290                 295                 300
```

```
Ile Gly Leu Arg Phe Asn Asp Pro Trp Asp Trp Asp Asn Ile Pro Ile
305                 310                 315                 320

Phe Val

<210> SEQ ID NO 4
<211> LENGTH: 324
<212> TYPE: PRT
<213> ORGANISM: Candida tropicalis

<400> SEQUENCE: 4

Met Ser Thr Thr Pro Thr Ile Pro Thr Ile Lys Leu Asn Ser Gly Tyr
1               5                   10                  15

Glu Met Pro Leu Val Gly Phe Gly Cys Trp Lys Val Asn Asn Glu Thr
            20                  25                  30

Ala Ala Asp Gln Ile Tyr Asn Ala Ile Lys Thr Gly Tyr Arg Leu Phe
        35                  40                  45

Asp Gly Ala Glu Asp Tyr Gly Asn Glu Lys Glu Val Gly Glu Gly Ile
    50                  55                  60

Asn Arg Ala Ile Lys Glu Gly Leu Val Lys Arg Glu Glu Leu Phe Ile
65                  70                  75                  80

Thr Ser Lys Leu Trp Asn Asn Phe His Asp Pro Lys Asn Val Glu Thr
                85                  90                  95

Ala Leu Asn Lys Thr Leu Ser Asp Leu Asn Leu Asp Tyr Val Asp Leu
            100                 105                 110

Phe Leu Ile His Phe Pro Ile Ala Phe Lys Phe Val Pro Ile Glu Glu
        115                 120                 125

Lys Tyr Pro Pro Gly Phe Tyr Cys Gly Asp Gly Asp Asn Phe His Tyr
    130                 135                 140

Glu Asp Val Pro Leu Leu Asp Thr Trp Lys Ala Leu Glu Lys Leu Val
145                 150                 155                 160

Glu Ala Gly Lys Ile Lys Ser Ile Gly Ile Ser Asn Phe Thr Gly Ala
                165                 170                 175

Leu Ile Tyr Asp Leu Ile Arg Gly Ala Thr Ile Lys Pro Ala Val Leu
            180                 185                 190

Gln Ile Glu His His Pro Tyr Leu Gln Gln Pro Lys Leu Ile Glu Tyr
        195                 200                 205

Val Gln Lys Ala Gly Ile Ala Ile Thr Gly Tyr Ser Ser Phe Gly Pro
    210                 215                 220

Gln Ser Phe Leu Glu Leu Glu Ser Lys Arg Ala Leu Asn Thr Pro Thr
225                 230                 235                 240

Leu Phe Glu His Glu Thr Ile Lys Ser Ile Ala Asp Lys His Gly Lys
                245                 250                 255

Ser Pro Ala Gln Val Leu Leu Arg Trp Ala Thr Gln Arg Asn Ile Ala
            260                 265                 270

Val Ile Pro Lys Ser Asn Asn Pro Glu Arg Leu Ala Gln Asn Leu Ser
        275                 280                 285

Val Val Asp Phe Asp Leu Thr Lys Asp Leu Asp Asn Ile Ala Lys
    290                 295                 300

Leu Asp Ile Gly Leu Arg Phe Asn Asp Pro Trp Asp Trp Asp Asn Ile
305                 310                 315                 320

Pro Ile Phe Val

<210> SEQ ID NO 5
<211> LENGTH: 324
<212> TYPE: PRT
```

<213> ORGANISM: Candida parapsilosis

<400> SEQUENCE: 5

Met Ser Thr Ala Thr Ala Ser Pro Ala Val Lys Leu Asn Ser Gly Tyr
1               5                   10                  15

Glu Ile Pro Leu Val Gly Phe Gly Cys Trp Lys Leu Thr Asn Asp Val
            20                  25                  30

Ala Ser Asp Gln Ile Tyr Arg Ala Ile Lys Ser Gly Tyr Arg Leu Phe
        35                  40                  45

Asp Gly Ala Glu Asp Tyr Ala Asn Glu Gln Glu Val Gly Glu Gly Ile
    50                  55                  60

Lys Arg Ala Ile Lys Glu Gly Ile Val Lys Arg Glu Glu Leu Phe Ile
65                  70                  75                  80

Thr Ser Lys Leu Trp Asn Ser Phe His Asp Lys Asn Val Glu Val
                85                  90                  95

Ala Leu Met Lys Thr Leu Ser Asp Leu Asn Leu Asp Tyr Val Asp Leu
            100                 105                 110

Phe Tyr Ile His Phe Pro Ile Ala Gln Lys Pro Val Pro Ile Glu Lys
        115                 120                 125

Lys Tyr Pro Pro Gly Phe Tyr Cys Gly Asp Gly Asp Lys Trp Ser Ile
    130                 135                 140

Glu Glu Val Pro Leu Leu Asp Thr Trp Arg Ala Leu Glu Lys Leu Val
145                 150                 155                 160

Asp Gln Gly Leu Ala Lys Ser Ile Gly Ile Ser Asn Phe Ser Ala Gln
            165                 170                 175

Leu Ile Tyr Asp Leu Ile Arg Gly Cys Thr Ile Lys Pro Val Ala Leu
        180                 185                 190

Gln Ile Glu His His Pro Tyr Leu Thr Gln Pro Lys Leu Val Glu Tyr
    195                 200                 205

Val Gln Leu His Asp Ile Gln Ile Thr Gly Tyr Ser Ser Phe Gly Pro
    210                 215                 220

Gln Ser Phe Leu Glu Met Asp Leu Lys Arg Ala Leu Asp Thr Pro Val
225                 230                 235                 240

Leu Leu Glu Glu Pro Thr Val Lys Ser Ile Ala Asp Lys His Gly Lys
            245                 250                 255

Ser Pro Ala Gln Val Leu Leu Arg Tyr Gln Thr Gln Arg Gly Ile Ala
        260                 265                 270

Val Ile Pro Arg Ser Asn Ser Pro Asp Arg Met Ala Gln Asn Leu Ser
    275                 280                 285

Val Ile Asp Phe Glu Leu Thr Gln Asp Leu Gln Ala Ile Ala Glu
    290                 295                 300

Leu Asp Cys Asn Leu Arg Phe Asn Glu Pro Trp Asp Phe Ser Asn Ile
305                 310                 315                 320

Pro Val Phe Val

<210> SEQ ID NO 6
<211> LENGTH: 319
<212> TYPE: PRT
<213> ORGANISM: Aspergillus niger

<400> SEQUENCE: 6

Met Ala Ser Pro Thr Val Lys Leu Asn Ser Gly Tyr Asp Met Pro Leu
1               5                   10                  15

Val Gly Phe Gly Leu Trp Lys Val Asn Asn Asp Thr Cys Ala Asp Gln
            20                  25                  30

-continued

Ile Tyr His Ala Ile Lys Glu Gly Tyr Arg Leu Phe Asp Gly Ala Cys
            35                  40                  45

Asp Tyr Gly Asn Glu Val Glu Ala Gly Gln Gly Ile Ala Arg Ala Ile
        50                  55                  60

Lys Asp Gly Leu Val Lys Arg Glu Glu Leu Phe Ile Val Ser Lys Leu
65                  70                  75                  80

Trp Asn Ser Phe His Asp Gly Asp Arg Val Glu Pro Ile Cys Arg Lys
                85                  90                  95

Gln Leu Ala Asp Trp Gly Ile Asp Tyr Phe Asp Leu Tyr Ile Val His
            100                 105                 110

Phe Pro Ile Ser Leu Lys Tyr Val Asp Pro Ala Val Arg Tyr Pro Pro
        115                 120                 125

Gly Trp Lys Ser Glu Lys Asp Glu Leu Glu Phe Gly Asn Ala Thr Ile
130                 135                 140

Gln Glu Thr Trp Thr Ala Met Glu Ser Leu Val Asp Lys Lys Leu Ala
145                 150                 155                 160

Arg Ser Ile Gly Ile Ser Asn Phe Ser Ala Gln Leu Val Met Asp Leu
                165                 170                 175

Leu Arg Tyr Ala Arg Ile Arg Pro Ala Thr Leu Gln Ile Glu His His
            180                 185                 190

Pro Tyr Leu Thr Gln Thr Arg Leu Val Glu Tyr Ala Gln Lys Glu Gly
        195                 200                 205

Leu Thr Val Thr Ala Tyr Ser Ser Phe Gly Pro Leu Ser Phe Leu Glu
210                 215                 220

Leu Ser Val Gln Asn Ala Val Asp Ser Pro Pro Leu Phe Glu His Gln
225                 230                 235                 240

Leu Val Lys Ser Ile Ala Glu Lys His Gly Arg Thr Pro Ala Gln Val
                245                 250                 255

Leu Leu Arg Trp Ala Thr Gln Arg Gly Ile Ala Val Ile Pro Lys Ser
            260                 265                 270

Asn Asn Pro Gln Arg Leu Lys Gln Asn Leu Asp Val Thr Gly Trp Asn
        275                 280                 285

Leu Glu Glu Glu Glu Ile Lys Ala Ile Ser Gly Leu Asp Arg Gly Leu
290                 295                 300

Arg Phe Asn Asp Pro Leu Gly Tyr Gly Leu Tyr Ala Pro Ile Phe
305                 310                 315

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtagctacgt cacatatggt tcctgctatc aagctc                                 36

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 8
ctgatagcgg atccctaacc gaaaatccag aggttctcag cggagaagta gttg      54
```

HIGHLY ACTIVE XYLOSE REDUCTASE FROM *NEUROSPORA CRASSA*

CROSS-REFERENCE TO RELATED PATENT APPLICATIONS

This patent application is a divisional of U.S. application Ser. No. 11/151,762, filed Jun. 14, 2005, which claims priority to U.S. provisional Application No. 60/579,710, filed Jun. 15, 2004, the contents of which applications are incorporated by reference in their entireties.

BACKGROUND

Xylose reductase (XR) catalyzes the first step in xylose metabolism, reducing the pentose sugar to xylitol with the concomitant oxidation of NAD(P)H to NAD(P). This enzyme is important at least in two areas: (1) xylose fermentation for ethanol production and (2) conversion of xylose into xylitol, which is a low calorie food additive. *N. crassa* was identified as able to convert plant biomass directly into ethanol and is known to possess D-xylose metabolizing enzymes.

Xylose reductase (XR) is an enzyme found commonly in yeast and fungal organisms often with several isozymes in the same species. This enzyme catalyzes the first step in the metabolism of D-xylose and other pentose sugars by reducing the linear aldehyde form of the sugar to xylitol (or a corresponding sugar alcohol). Xylitol can then be oxidized to xylulose by NAD-dependent xylitol dehydrogenase and phosphorylated by D-xylulokinase. The resulting sugar phosphate can enter the pentose phosphate pathway. The reversible reduction of xylitol by XR occurs concomitantly with NAD(P)H oxidation. In general, XR is specific for NADPH, but in some cases it utilizes both NADPH and NADH and in at least one case prefers NADH over NADPH. The different forms of XR in the same species usually have different cofactor preferences and they are likely needed to maintain the redox balance between nicotinamide cofactors under a variety of growth conditions. In order to maintain this balance under anaerobic conditions, XR is likely to be NADH-dependent because the enzyme in the following step (xylitol dehydrogenase) is NAD specific. However, under aerobic conditions either cofactor can be used since cofactors can be regenerated. Some yeast species have solved this problem by utilizing one form of XR with dual cofactor specificity.

Based on sequence and structure similarities, fungal and yeast XRs have been classified as members of the aldo-keto reductase (AKR) enzyme superfamily and more specifically, they belong to the aldose reductase family (EC 1.1.1.21). AKRs have been studied for their ability to detoxify reactive carbonyl compounds, control osmotic pressure by regulating intracellular polyols, and of clinical interest, in diabetic complications resulting from aldose reductase (AR) activity in hyperglycemic patients. The majority of the more than 100 known AKRs are monomeric, however most XRs are homodimers. Other AKRs have quaternary structural organization, but the dimeric interface of XR is unique. Most AKRs favor the reaction in which the carbonyl substrate is reduced. However, their substrate specificity is often very flexible. This is true for XRs as well, which favor production of xylitol and NAD(P) and can often host a variety of other aldehyde substrates.

Although human AR has been studied for decades due to its formation of high levels of polyols in hyperglycemic tissues of diabetic patients, XR in yeast has gained interest for an entirely different reason. D-xylose is known to be among the most abundant sugar constituents of plant biomass as the predominant subunit of hemicelluloses like xylan and xyloglucans. Because XR is critical to xylose utilization by yeast and fungi, this enzyme is important in the fermentation of plant biomass to ethanol. Enhancing the fermentation efficiency is of interest because this fermentation could convert agricultural byproducts and waste into a useful energy source. Improving xylose metabolism may result from recombinant expression of xylose utilizing genes including XR. Additionally, XR may be applied to the production of xylitol, a non-caloric anticariogenic natural sweetener. In this way, XR is linked to human AR because xylitol is a possible sugar substitute for diabetics. Its metabolism is not insulin dependent. An economical means of producing xylitol from xylose in vitro utilizing an XR and a cofactor regeneration system has been proposed by Nidetzky et al. (1996). Similar processes have also been proposed by Ikemi et al. (1990) for converting glucose into sorbitol. Therefore highly active XRs are desirable both for improving xylose metabolism for fermenting yeast and as a reliable low cost source of pure XR for in vitro xylitol production.

Xylitol is usually prepared by processes in which a xylan-containing material is first hydrolysed to produce a mixture of monosaccharides, including xylose. The xylose is then converted to xylitol, generally in a chemical process using a nickel catalyst such as Raney-nickel.

The primary genetic sequences of many XRs have been determined and several have subsequently been cloned and expressed in a variety of hosts. However, a significant lag between genome sequence information and biochemical information has left a large number of proteins, including possible XRs, unidentified. In 2003, the entire 40 Mb genome of the common fungi *Neurospora crassa* was sequenced. *N. crassa* has been the subject of over 70 years of research as a model organism for multicellular eukaryotes. A useful characteristic of this organism is that it can directly convert plant biomass to ethanol because it produces cellulase and xylanse enzymes. D-xylose metabolizing enzymes are related to xylose fermentation.

SUMMARY OF THE DISCLOSURE

A highly active xylose reductase (XR) isolated and purified from *Neurospora crassa* (*N. Crassa*) is useful in the production of ethanol and xylitol from xylose. Methods and compositions relate xylose reductase and its use in the production of commercially important compounds such as ethanol and xylitol.

A xylose reductase from *N. crassa* expressed in a heterologous host such as *E. coli*, exhibits high activity and efficiency.

A xylose reductase (XR) encoding gene in *N. crassa* was identified by a BLAST search, was cloned by RT-PCR and expressed heterologously in *E. coli*. One gene was isolated from the 10,082 predicted genes in *N. crassa* that encoded a hypothetical protein with significant sequence homology to XRs from other species. This gene was subsequently cloned, expressed heterologously, and purified in a simple one step protocol with high yield. The resulting protein is characterized and compared with other XRs, as described herein.

The *N. crassa* XR (ncXR) was purified as a $His_6$-tag (SEQ ID NO: 1) fusion, determined to be a dimer with a subunit mass of 38,381 Da (with $His_6$-tag; SEQ ID NO: 1) and further characterized. The enzyme proved to be highly active with NADPH and xylose with a $k_{cat}$ of 60 $s^{-1}$, with low $K_M$ values for both xylose (34 mM) and NADPH (1.8 µM). The enzyme also showed activity with NADH with 100-fold lower catalytic efficiency and activity with other sugar substrates including D-ribose, D-arabinos, D-galactose, and D-glucose.

Homology modeling of the protein was performed and it was determined to fit very well into the $(\beta/\alpha)_8$ barrel fold and was very similar in structure to *C. tenuis* XR. The enzyme was also thermally stable with an optimal temperature between 45 and 55° C. and a half-life of thermal inactivation of 71 minutes at 40° C. The disclosed enzyme is a highly active and catalytically efficient XR. Additionally, the stability and high purification yields (13 mg/g *E. coli*) make it a useful enzyme for in vitro production of xylitol or metabolic engineering for xylose fermentation.

A purified xylose reductase isolated from *Neurospara crasa*. The xylose includes an amino acid sequence in accord with FIG. 1 or a sequence that is at least 90% similar.

The purified xylose reductase is at least 95% pure. The xylose reductase of further includes the following characteristics:
  (a) has a molecular weight of about 36 kDa;
  (b) is active with NADH and NADPH as cofactors with a preference for NADPH;
  (c) has D-ribose, L-arabinase, D-galactase and D-glucose as substrates;
  (d) has a pH optima in the range of about pH 4.5-pH 6.0;
  (e) has a Km of 34 mM for xylose and 1.8 µM for NADPH; and
  (f) is stable at room temperature.

The xylose reductase is recombinant and may include a fusion protein.

The xylose reductase is purified from a heterologous host. The heterologous host is selected from the group consisting of bacteria, yeast, and plants.

In an embodiment, the purified xylose reductase is used to produce xylitol. The production of xylitol may be in a membrane reactor. The production of xylitol in the membrane reactor is continuous.

In an embodiment, the production of xylitol utilizes a phosphite dehydrogenase-based NADP regeneration system.

The purified xylose reductase is used to produce a sugar alcohol. The sugar alcohol is sorbitol. The purified xylose reductase is used to produce ethanol. The production of ethanol is by fermentation.

The purified xylose reductase is used to metabolically enhance an organism used for fermentation of a plant biomass to produce ethanol.

A method of producing ethanol includes the steps of:
  (a) obtaining a highly active form of xylose reductase comprising an amino acid sequence of a *Neurospora crassa* xylose reductase as in FIG. 1 or an amino acid sequence that is 90% similar to the *Neurospora crassa* xylose reductase; and
  (b) providing conditions to produce ethanol from a xylose containing medium.

A method of producing xylitol includes the steps of:
  (a) obtaining a highly active form of xylose reductase comprising an amino acid sequence of a *Neurospora crassa* xylose reductase as in FIG. 1 or an amino acid sequence that is 90% similar to the *Neurospora crassa* xylose reductase; and
  (b) providing conditions to produce xylitol from a xylose containing medium.

The xylose reductase is expressed in a heterologous host in a fermentation process to produce ethanol. The method further includes the use of a phosphite dehydrogenase (PTDH) for co-factor regeneration.

A heterologous host expressing xylose reductase that includes an amino acid sequence of a *Neurospora crassa* xylose reductase as in FIG. 1 or an amino acid sequence that is 90% similar to the *Neurospora crassa* xylose reductase.

The heterologous host is selected from the group consisting of *Escherichia coli*, *Saccharomyces cerevisiae*, a plant cell and other similar hosts known to those of skill in the art.

DEFINITIONS AND ABBREVIATIONS

Aldo-keto reductase enzyme family (AKR)

Aldose reductase (AR)

Dithiothreitol (DTT)

Ethylenediaminetetraacetic acid (EDTA)

Electrospray ionization quadrupole time of flight mass spectrometry (ESI-Q-TOF)

Fast performance liquid chromatography (FPLC)

High performance liquid chromatography (HPLC)

Isopropyl-β-D-thiogalactopyranoside (IPTG)

Luria-Bertani broth (LB)

Maximal velocity ($V_{max}$)

Michaelis kinetic constant ($K_M$)

MOE (Molecular Operating Environment)

National Center for Biotechnology Information (NCBI)

Nicotinamide adenine dinucleotide oxidized (NAD)

Nicotinamide adenine dinucleotide reduced (NADH)

Nicotinamide adenine dinucleotide phosphate oxidized (NADP)

Nicotinamide adenine dinucleotide phosphate reduced (NADPH)

Reverse transcription polymerase chain reaction (RT-PCR)

Root mean square deviation (RMS)

Sodium dodecyl sulfate polyacrylamide gel electrophoresis (SDS-PAGE)

Turnover numer ($k_{cat}$)

Xylose reductase (XR)

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE DRAWINGS

FIG. 1 shows amino acid sequence alignment of *N. crassa* xylose reductase (XR) with four other closely related XR sequences from fungi and yeast (SEQ ID NOS: 2-6, respectively, in order of appearance). Residues highlighted in gray represent the conserved tyrosine, lysine, and aspartate that make up the active site catalytic triad and the histidine involved in positioning of the aldehyde substrate.

DETAILED DESCRIPTION OF THE DISCLOSURE

Figure 2:
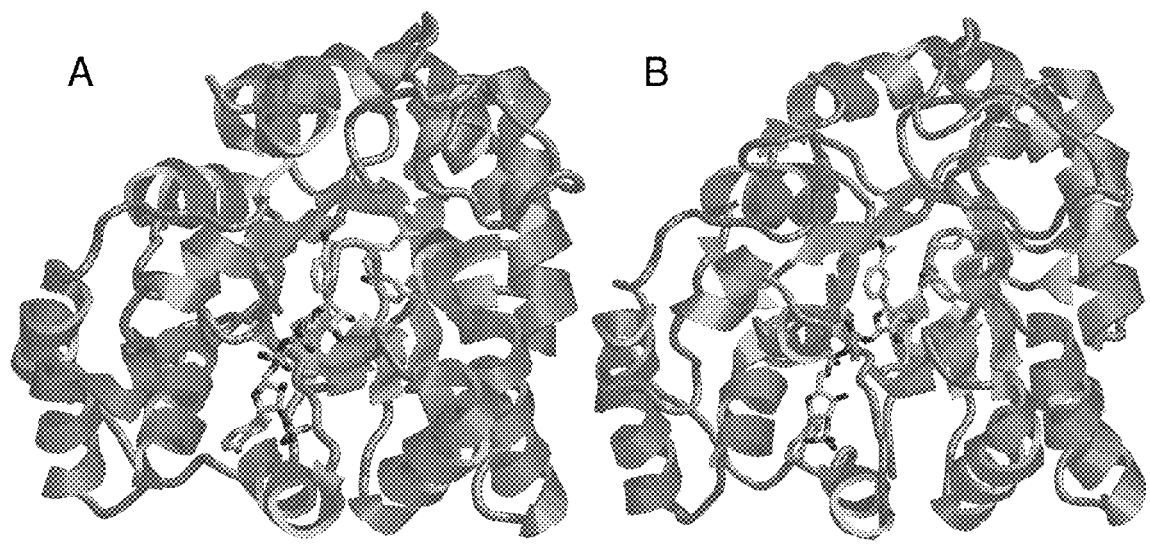
FIG. 2 shows a (A) crystal structure of *C. tenuis* XR with bound NADPH (1K8C); (B) Homology model of ncXR with bound NADPH built using Insight II (Accelrys Inc.; San Diego, Calif.) and MOE (Chemical Computing Group, Montreal, Canada). The $(\beta/\alpha)_8$ barrel is the catalytic tyrosine and lysine as well as the bound cofactors are indicated by atom type. The locations of the α-carbons in the two structures differ by only 0.486 Å RMS deviation.

A gene encoding a xylose reductase (XR) was identified in *N. crassa* 10333, a filamentous fungus capable of metabolizing xylose. The gene was identified by BLAST search as a hypothetical protein. This gene was transcribed into mRNA by the presence of an RT-PCR product with the predicted sequence, which was cloned and heterologously expressed in *E. coli*. The isolated gene encoded a protein sequence that was similar to other D-xylose reductases such as *C. tenuis* (1MI3) and had lower sequence similarity to other members of the AKR superfamily including human AR (2ALR).

Homology to the aforementioned proteins of known structure was utilized in constructing a high quality homology model. Many important residues were conserved with regards to orientation and location between *C. tenuis* XR and ncXR. Among these were the catalytic triad of Tyr 52, Asp 47, and Lys 81 (*C. tenuis* numbering). Lys and Asp likely serve to depress the pKa of the Tyr phenolic oxygen so that it functions as the general acid. The orientation of His-114 is preserved, which is believed to position the carbonyl of the substrate such that the C4 hydride of NAD(P)H attacks the electrophilic carbonyl carbon. The xylose binding pocket is very hydrophobic with great similarity to *C. tenuis*. The structures share similar locations for (ncXR numbering) Trp 21, Trp 80, Phe 112, and Phe 225, but ncXR had the additional polar residue Asn 167 near the binding pocket while lacking hydrophobic residues corresponding to the Phe 132 and Trp 315 of *C. tenuis* XR. These differences may cause the increased affinity (assumed from $K_{M,xylose}$ values) for xylose by *N. crassa* over *C. tenuis* XR. The $K_{M,NADPH}$ values for of *C. tenuis* XR and ncXR are among the lowest reported for XRs (Table 3). Nearly all of the 19 residues previously found to be involved in binding NADPH are conserved. Differences in these residues include the replacement of Cys 23 in *C. tenuis* XR with Leu 20 in ncXR with additional contacts made by Asn 310, Ser 28 and the amide carbonyl of Ile 269 which were previously determined to be important in *C. tenuis* XR.

The cloned *N. crassa* XR is a dimer in its native recombinant form. However, it does not share significant sequence homology with the previously determined dimerization domains for *C. tenuis, P. stipitus*, and *C. tropicalis*. In particular the C-terminal region after residue 308 of ncXR is different from other dimeric yeast XRs. Other regions of sequence homology in helix 5 and helix 6 previously implicated in dimerization also are not found in the nxXR sequence. The overall fold and region of dimerization in *C. tenuis* is similar in the ncXR homology model. It is likely that ncXR forms a dimer with the same type of interface, but a with a different consensus sequence.

One XR has previously been reported from *N. crassa* NCIM 870 (Rowat et al., 1996). However, there are significant differences between the XR disclosed herein and the XR previously reported. The subunit weights and apparent native weights are significantly different between these two enzymes; the previously isolated other enzyme was 29 and 60 kDa respectively, while ncXR was determined to be 38.4 kDa (36.3 kDa without $His_6$-tag; SEQ ID NO: 1) and 53 kDa respectively. Furthermore, the $k_{cat}$ of NADPH-dependent xylose reduction was about 16% higher and the $K_{M,NADPH}$ was 5-fold higher for *N. crassa* XR previously isolated by Rawat and Rao (1996). This results in a 4-fold higher catalytic efficiency with respect to NADPH for the enzyme isolated in this work. Additionally, the XR isolated by Rawat and Rao showed no activity with NADH as the reducing cofactor, while the XR disclosed herein can utilize NADH with a $k_{cat}$ of 310 min$^{-1}$ and a $K_{M,NADH}$ of 16 µM (Table 1). Furthermore, the two enzymes differ by their pH optimums and $K_M$ values for xylose.

Table 3 displays the kinetic characteristics of seven other purified and characterized XRs from *C. intermedia, C. parapsilosis, C. tropicalis, C. tenuis, P. tannophilus, P. stipitus*, and *S. cerevisiae*. All but two of these enzymes are dimers in their native form and they all have subunit molecular weights between 33 and 38 kDa. Compared to these enzymes, the disclosed ncXR has a higher $k_{cat}$, catalytic efficiency with respect to xylose, and catalytic efficiency with respect to NADPH. The $k_{cat}$ is more than 2-fold higher than a NADPH-dependent enzyme (*P. stipitus*) (Verduyn et al. 1985 and 16% higher than the NADH-dependent *C. parapsilosis* XR. The catalytic efficiency with respect to NADPH was more than 7-fold greater than the next closest enzyme (*C. tenuis* XR) and more than 11-fold greater than any of the other enzymes. The NADH-dependent XR $k_{cat}$ (310 min$^{-1}$) for ncXR was 10-fold lower than that of the *C. parapsilosis* XR (3100 min$^{-1}$) and about 3-fold lower than that of *C. tenuis* XR (1100 min$^{-1}$), but it still retains a reasonable $K_{M,NADH}$ of 16 µM (Table 1).

Figure 5:
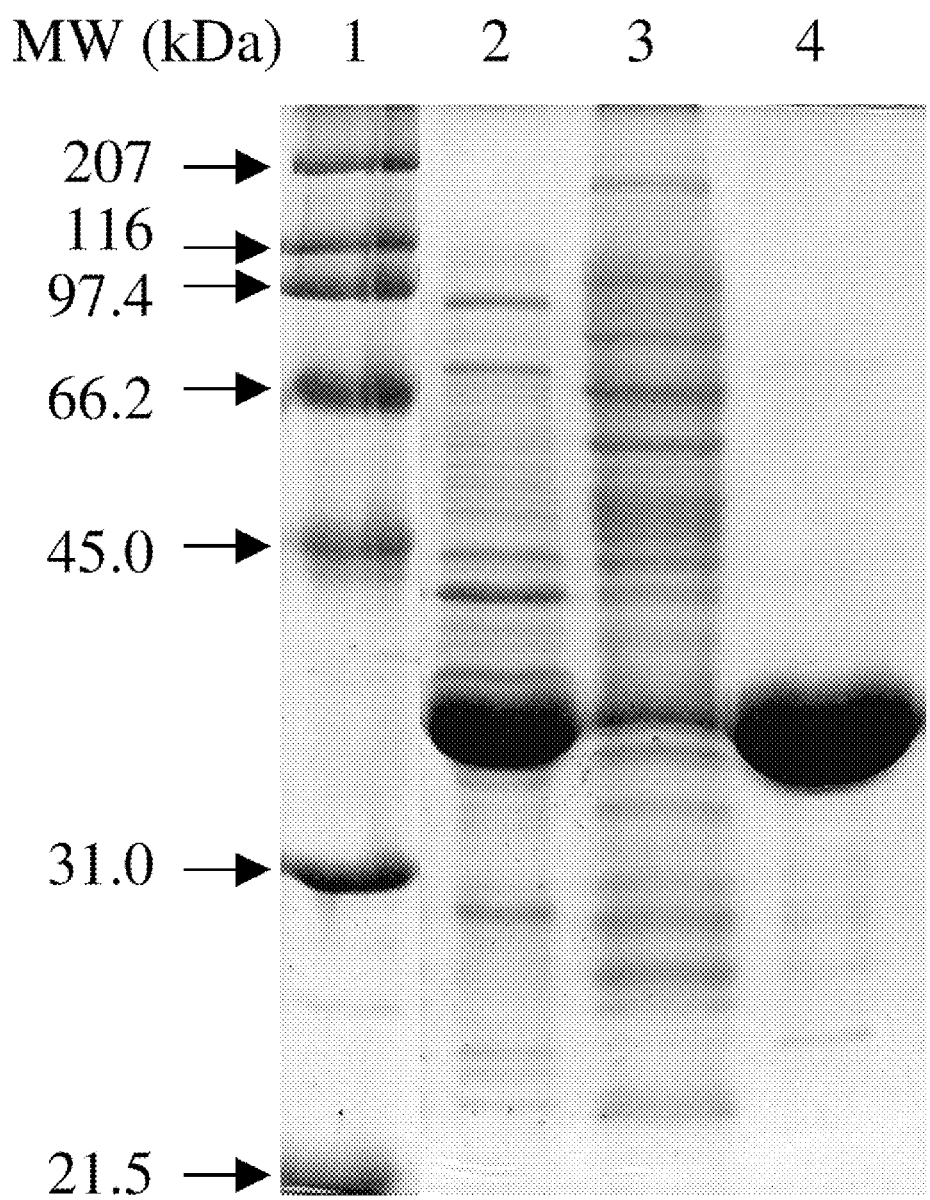
FIG. 5 shows gel images demonstrating purification of heterologously expressed XR-$His_6$-tag (SEQ ID NO: 1) fusion protein. Lane 1 contains the molecular weight marker, lane 2 contains the soluble fraction of the induced cells, lane 3 contains the flow through during the purification, and lane 4 contains the final purified XR. Soluble expression of the XR reaches very high levels of around 50% of the total cellular proteins. The purified enzyme is greater than 95% pure and can be isolated in yields of more than 13 mg/g of wet cells.

The extremely high activity and efficiency of this newly isolated protein makes it useful in xylose metabolic enhancement. This enzyme is contemplated to have even greater utility in the in vitro production of xylitol (or other sugar alcohols like sorbitol). It is additionally beneficial that the ncXR is expressed in *E. coli* in unusually high yields. The heterologous expression level of XR is greater than 50% of the total cellular protein (FIG. 5). The yield of this protein was exceedingly high at greater than 13 mg of pure protein per g of induced cells. This would subsequently reduce the cost of the purified enzyme for in vitro utilization significantly. Furthermore, this enzyme is very stable at room temperature and is active at a fairly broad pH range making it suitable for enzymatic membrane reactor use. Xylose can be converted into xylitol by XR, which is subsequently converted into ethanol by xylitol dehydrogenase, see U.S. Pat. No. 6,582, 944, incorporated herein by reference.

Suitable heterologous hosts include yeast, bacteria and plant cells engineered to express the xylose reductase from *N. crassa* disclosed herein. Other enzyme components such as xylitol dehydrogenase or any other necessary enzymes needed for the production of ethanol or xylitol can also be engineered in the heterologous hosts.

EXAMPLES

The following examples are to be considered as exemplary and not restrictive in character.

Example 1

Identification of xyl1 gene in *N. crassa*. Protein sequences were downloaded from NCBI for the *C. tenuis* (gb|AAC25601.1|) and *C. tropicalis* I-II (dbj|BAA19476.1|) xylose reductases. These sequences were individually used in a protein-protein BLAST search against the *N. crassa* genome. Several hypothetical protein sequences had more than 35% sequence identity with both *C. tenuis* and *C. tropicalis* XRs including NCU 08384.1 (gb|EAA34695.1|) (52.5% average identity), NCU 01906.1 (gb|EAA36301.1|) (36% average identity), NCU 04510.1 (gb|EAA27685.1|) (35.5% average identity), and NCU 04923.1 (gb|EAA30135.1|) (39% average identity). The sequence with the highest homology in both searches was hypothetical protein NCU 08384.1 (gb|EAA34695.1|). This protein sequence was used in a subsequent BLAST search against the non-redundant gene database. Out of the top ten hits, 6 sequences were identified as D-xylose reductases and the remaining 4 were hypothetical proteins without any assigned function. NCU 08384.1, which will be referred to as *N. crassa* XR (ncXR) herein, had significant homology with other xylose reductases as displayed by the sequence alignment in FIG. 1. ncXR has 66% sequence identity with *Aspergillus niger* XR (gb|AAF61912.1|), 53% sequence identity with *C. tropicalis* XR, 52% sequence identity with *C. tenuis* XR, and 51% sequence identity with *Candida parapsilosis* XR (gb|AAO91803.1|). Among the residues shared in all of these sequences were the catalytic triad of lysine, tyrosine, and aspartate along with a conserved histidine that positions the substrate, which are shaded in gray in FIG. 1.

Example 2

Homology Modeling. There is a high-resolution x-ray crystal structures available for *C. tenuis* XR complexed with NADH (1MI3). Additionally, the structure of human aldehyde reductase (2ALR) has been solved by X-ray crystallography and it shares 40% sequence identity with ncXR. These structures were chosen as templates because they both had better than 40% sequence identity with ncXR, shared the same basic $(\alpha/\beta)_8$ barrel fold, and had high resolution structures. The structural homology model was built as disclosed herein, resulting in a model structure of ncXR. The completed model was very similar to the *C. tenuis* crystal structure in overall fold and binding of coenzyme as depicted in FIG. 2. The RMS deviation between the α-carbons of the backbone between *C. tenuis* XR and the model structure was only 0.486 Å with the most obvious differences being between the C-terminal residues after 311 and 308 of *C. tenuis* x-ray structure and ncXR model respectively. If these residues are not taken into account, the RMS deviation is reduced to 0.339 Å. To further verify the model, the overall fold was checked using Profiles3-D (Insight II) and the allowed states for φ and ψ angles and bond distances were checked using ProStat (Insight II), both under default conditions. The Profiles3-D (Insight II, default parameters) check resulted in a self-compatability score of 99.3%, which compares well to the scores of 98.5% and 100% for the coordinants from 2ALR and 1MI3 respectively. The Prostat check of φ and ψ angles were determined to be 88.1% within their core expected values, comparing well to the 86.0% and 86.4% for the same analysis of PDB structures 2ALR and 1MI3, respectively.

As seen in FIG. 2B, oriented near the nicotinamide ring are residues Lys 78 and Tyr 49, which together with Asp 44 make up the active site triad. These residues correspond well in location and orientation with Lys 81, Tyr 52 and Asp 47 of *C. tenuis* XR as seen in FIG. 2A. Furthermore, other residues involved in binding and specificity for the nicotinamide cofactor are very similar in orientation and location between the model and 1MI3.

Example 3

Cloning and recombinant expression of *N. crassa* XR. The gene (AABX01000063) encoding the identified *N. crassa* XR was predicted from the whole genome sequencing in 2003. The total gene complete with two introns is 1402 bp and the predicted introns cover bases 143-459 and 1251-1366.

Figure 3:
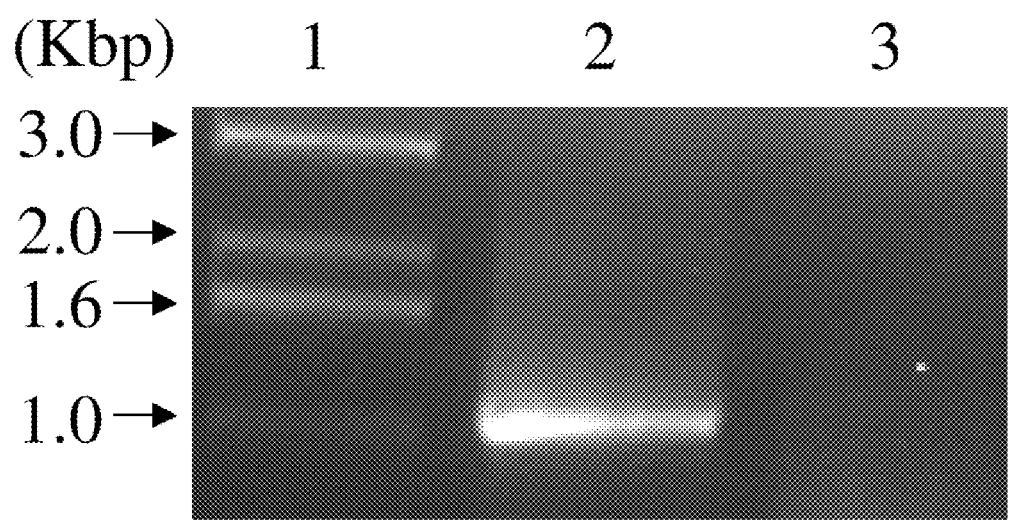
FIG. 3 RT-PCR product of the XR gene. Lane 1 shows the DNA base pair ladder. Lane 2 is the RT-PCR product amplified from *N. crassa* total RNA. Lane 3 is the control in which there was no reverse transcription. The approximately 1 kb product in Lane 2 was the expected size for the 969 bp *N. crassa* XR gene plus the extra primer length for cloning. This product was subsequently sequenced and determined to be the desired gene.

With these introns removed, the gene is 969 bp long with the second splice site just 36 bp from the end of the gene. To ease in the cloning of the gene with the introns removed and to verify that the gene is indeed expressed as an mRNA, RT-PCR was utilized. The total RNA from *N. crassa* was isolated after induction with xylose and then used in an RT-PCR to amplify the XR gene from the mRNA as discussed in the Materials and Methods. Because the final exon was just 36 bp, the reverse primer for the RT-PCR encoded the entire exon plus four residues of the previous exon, such that only the processed mRNA with introns removed would be amplified. FIG. 3 shows the RT-PCR product obtained that is approximately 1 kb while the control reaction without reverse transcriptase activity had no such product. This RT-PCR product was subsequently sequenced and found to be identical to the predicted 969 bp processed mRNA sequence.

The 969 bp XR gene was subsequently digested and ligated into two high copy overexpression vectors: pET15b and pET26b. The first vector (pET15b) encoded the protein as an N-terminal $His_6$-Tag (SEQ ID NO: 1) fusion with a thrombin cleavage site between the tag and the inserted gene, while the second vector (pET26b) encoded the protein without a tag. Two vectors were used to compare XR activity with and without the $His_6$-tag (SEQ ID NO: 1) because XRs are not typically purified with fusion tags. Positive clones were identified by cell lysate assay as described in the Material and Methods section and subsequently verified by sequencing.

Figure 4:
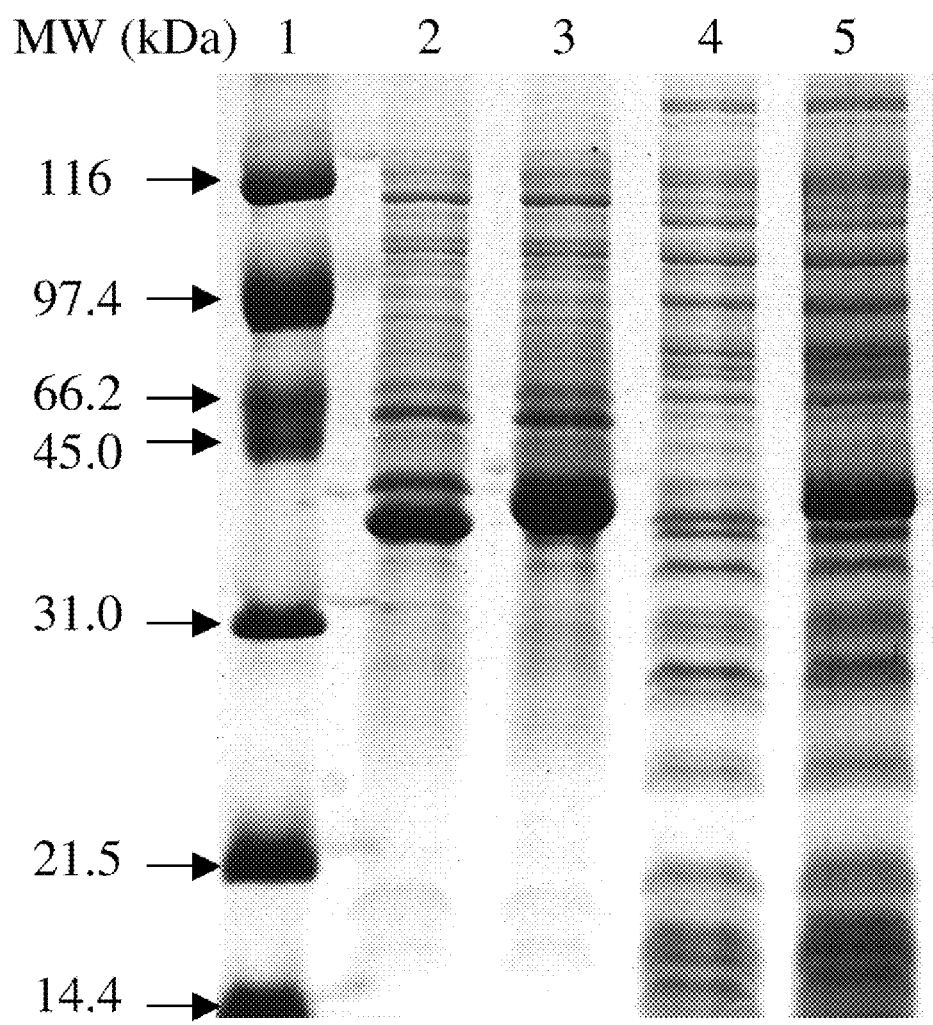
FIG. 4 shows gels images illustrating comparative expression of XR with and without a $His_6$-tag (SEQ ID NO: 1) in *E. Coli* BL21 (DE3). Lane 1 contains the MW marker. Lanes 2 and 4 contain the respective soluble and insoluble fractions from induced cells harboring pET26b-XR without $His_6$-tag (SEQ ID NO: 1). Lane 3 and 5 contain the respective soluble and insoluble fractions from induced cells harboring pET15b-XR as a $His_6$-tag (SEQ ID NO: 1) fusion. Soluble expression is very high with both constructs and is slightly better with the $His_6$-tag (SEQ ID NO: 1). However, there is also some insoluble expression with the $His_6$-tag (SEQ ID NO: 1).

Cell lysates of the verified clones of *E. coli* BL21 (DE3) expressing either the $His_6$-tagged (SEQ ID NO: 1) (pET15b) or non-tagged protein (pET26b) were again prepared and assayed as described in Materials and Methods, however samples of induced cells were kept for SDS-PAGE analysis. These samples were split into soluble and insoluble fractions using Bugbuster HT™ as the lysis reagent following the manufacturer's recommendations. The soluble and insoluble fractions were subsequently separated by SDS-PAGE (FIG. 4). Both tagged and non-tagged constructs seemed to produce soluble XR at greater than 25% of the total cellular protein. There was approximately 20% more soluble protein for the $His_6$-tagged (SEQ ID NO: 1) XR than the non-tagged XR as determined by densitometery. When the cell lysate activity was normalized with the soluble protein expression from FIG. 4, the non-tagged XR had about 25% higher specific activity than the tagged XR. However, due to the higher expression level of the tagged XR the two constructs had about the same lysate activity. The tagged XR also produced a moderate amount of insoluble inclusion bodies while the non-tagged XR appeared to be completely soluble.

Example 4

IMAC purification of *N. Crassa* XR. Despite the modestly lowered activity and solubility of the $His_6$-tagged (SEQ ID NO: 1) XR, it was chosen for purification and characterization. This choice was made due to the higher expression level of tagged XR, in addition to the ease of purifying $His_6$-tagged (SEQ ID NO: 1) proteins in high yield by Immobilized Metal Affinity Chromatography (IMAC). A 1.5 l culture of *E. coli* BL21 (DE3) containing the pET15b-XR was grown, induced and harvested as discussed in Materials and Methods resulting in about 5 g wet cell mass. Following IMAC purification using a 10 ml column of Talon™ resin freshly charged with $Co^{2+}$ and concentration and desalting, approximately 25 ml of 2.7 mg/ml XR was obtained. Final yield of protein was 68 mg of protein or 45 mg per liter of culture. Samples of the induced cells, column flow through, and purified protein were analyzed by SDS-PAGE (FIG. 5). The induced cells showed soluble XR expression that accounted for nearly 50% of the total cellular protein. The purified protein was greater than 95% pure with very little lost in the flow through. The approximate molecular mass of the protein subunit estimated from the gel was ~37 kDa, corresponding well to the predicted subunit mass.

Example 5

Protein mass and quaternary structure of XR. To determine the molecular weight of the subunit accurately, ESI-Q-TOF mass spectrometry was performed at the Mass Spectrometry Laboratory at University of Illinois. The highest abundance peak had a value of 38,381 m/z with a second peak of 20% abundance of 38,558 m/z. The first peak corresponds exactly with the predicted molecular mass for $His_6$-tagged (SEQ ID NO: 1) XR with the N-terminal formyl methionine removed, whereas the second peak corresponds well to the predicted molecular mass for $His_6$-tagged (SEQ ID NO: 1) XR with an N-terminal formyl methionine (38,541 Da) or with the N-terminal acetylated methionine (38,555 Da). Additionally, there is a $2M^+$ peak of about 15% abundance at 76,761 m/z, which corresponds well with the mass of the dimeric form of the enzyme (76,762 Da).

Figure 6:
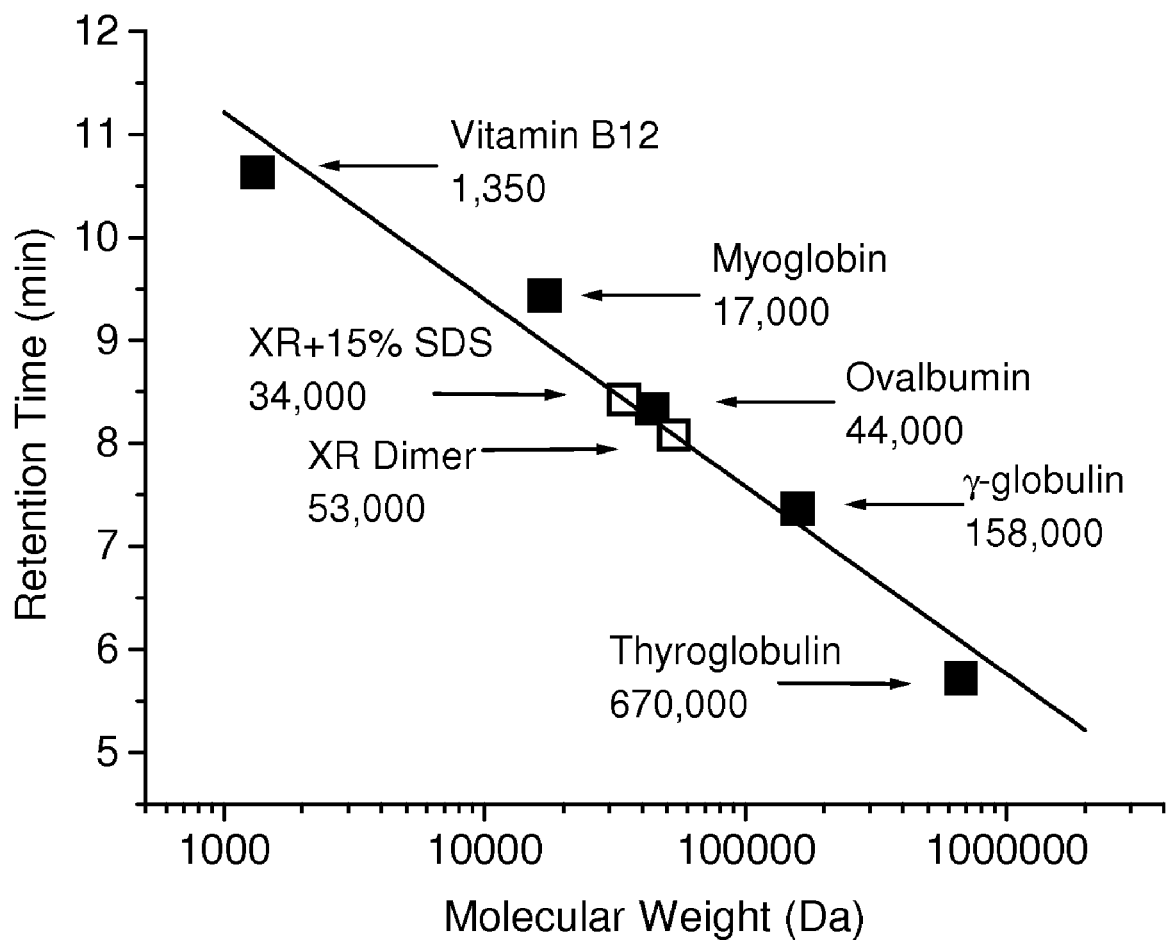
FIG. 6 shows results of HPLC size exclusion chromatography. A size exclusion standard was used to calibrate a Bio-Sil SEC-250, 300×7.8 mm column with a mobile phase of 0.1 M $NaPO_3$, 0.15 M NaCl, 0.01 M $NaN_3$, pH 6.8 at a flow rate of 1 ml/min. The standard proteins are represented by (■). XR samples (□) with and without 15% SDS were injected separately and fitted to the standard curve.

To further verify the quaternary structure of XR, HPLC size exclusion chromatography was performed. A standard solution containing five native weight markers was used to standardize the retention time as a function of native weight (FIG. 6) in two identical separate runs. XR was subsequently injected onto the column twice and it eluted as a single peak with an average retention time of 8.08 minutes. The molecular mass calculated from the standard curve is approximately 53 kDa. In an attempt to induce monomerization of XR, a sample was prepared in 15% SDS at room temperature. This sample also eluted as a single peak, however this time the retention time was 8.43 minutes corresponding to a molecular mass of approximately 34 kDa. This suggests that the native XR is a dimer with an apparent size of 1.6 times the monomer and can be dissociated into monomers by the addition of SDS at room temperature without significant denaturation.

Example 6

Determination of kinetic constants of xylose reductase. Purified *N. crassa* XR was determined to be active with both NADH and NADPH as the cofactor. To determine the effect of removal of the $His_6$-tag (SEQ ID NO: 1) the purified XR was incubated with and without thrombin at 4° C. overnight. The thrombin cleavage site leaves three amino acids (GSH) attached to the N-terminus of the XR sequence. Complete cleavage of the 2.1 kDa tag was verified by comparing the samples with SDS-PAGE. The specific activity of the cleaved and noncleaved samples was compared. It was determined that removal of the $His_6$-tag (SEQ ID NO: 1) enhanced activity by about 16%. Since there was not a large difference in activity and the tag is predicted to be distant to the active site, the tagged enzyme was used in all subsequent assays.

Michaelis-Menten constants ($K_M$) were determined for both cofactors as well as for xylose with either cofactor. The maximum turnover number ($k_{cat}$) was also determined with both cofactors. NADPH concentrations were varied from 0.5 to 20 μM and NADH concentrations were varied from 10 to 230 μM, while keeping xylose concentration at 300 mM. Xylose concentrations were varied from 10 to 250 mM while either cofactor concentration was held at 160 μM. *N. crassa* XR displayed typical Michaelis-Menten type kinetics with respect to all substrates for the reduction of xylose. *N. crassa*

XR clearly favors NADPH over NADH with a 100-fold better catalytic efficiency ($k_{cat}/K_M$). This is both a function of a higher $k_{cat}$ (3600 min$^{-1}$ compared to 312 min$^{-1}$) and lower $K_M$ (1.8 μM compared to 16 μM) for NADPH versus NADH. The $K_M$ value for xylose is not significantly changed from one cofactor to the other. The catalytic efficiency and turnover number are both very high for *N. crassa* XR in comparison to XRs from other sources.

Example 7

Analysis of substrate specificity. D-Ribose, L-arabinose, D-arabinose, D-galactose, sucrose, D-glucose, and D-fructose were all examined as alternative substrates for *N. crassa* XR with NADPH as the cofactor. D-Ribose, L-arabinose, D-galactose, and D-glucose all acted as substrates, while D-arabinose, D-fructose, and sucrose did not act as substrates. The $K_M$ and $k_{cat}$ values were determined for each substrate that showed activity (Table 2). All sugar substrates were reduced at a slower $k_{cat}$ than xylose, however the $k_{cat}$ with D-ribose was only slower by 13%. The slowest substrate turnover occurred with D-glucose with a $k_{cat}$ of 1320 min$^{-1}$, which was also the substrate with the highest $K_M$ at 360 mM. Five carbon sugars generally acted as better substrates, both with catalytic efficiencies 41% that of xylose. The catalytic activity was less than 10% that of xylose for both six carbon sugars showing activity.

Example 8

Figure 7:
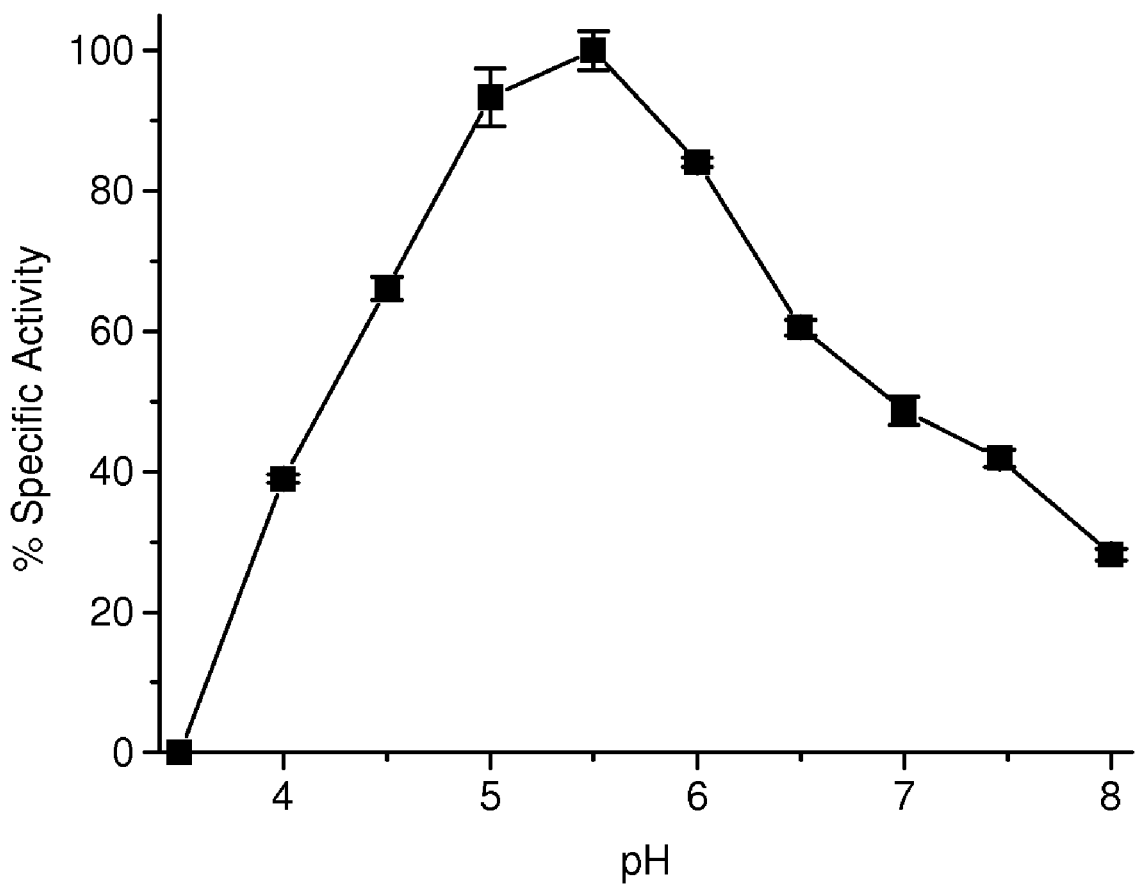
FIG. 7 is a pH rate profile. Saturating concentrations of 1 M xylose and 200 mM NADPH were used to measure the activity in a universal buffer at various pH values from 4.0 to 8.0.

Determination of pH rate profile. In order to determine the optimal pH and range for activity, a pH rate profile was obtained. Saturating concentrations of NADPH and xylose were prepared in universal buffer at various pH values from 4.0 to 8.0. The normalized specific activity was then plotted against pH as depicted in FIG. 7. The pH range for ncXR was large with activity above 25% from pH 4.0 to pH 8.0. The pH optima was around pH 5.5 and greater than 60% of the activity remained for the 2 pH unit span from 4.5 to 6.5. The inactivating protonation event happening between pH 4 and 5 may be due to protonation of Asp 44 of the catalytic triad, while the inactivating deprotonation event between pH 6 and 8 would most likely correspond to the deprotonation of the catalytic residue Tyr 48. The pH optimum is slightly lower than many of those previously determined (Table 3), however the profile is very similar to many other XRs.

Example 9

Figure 8:
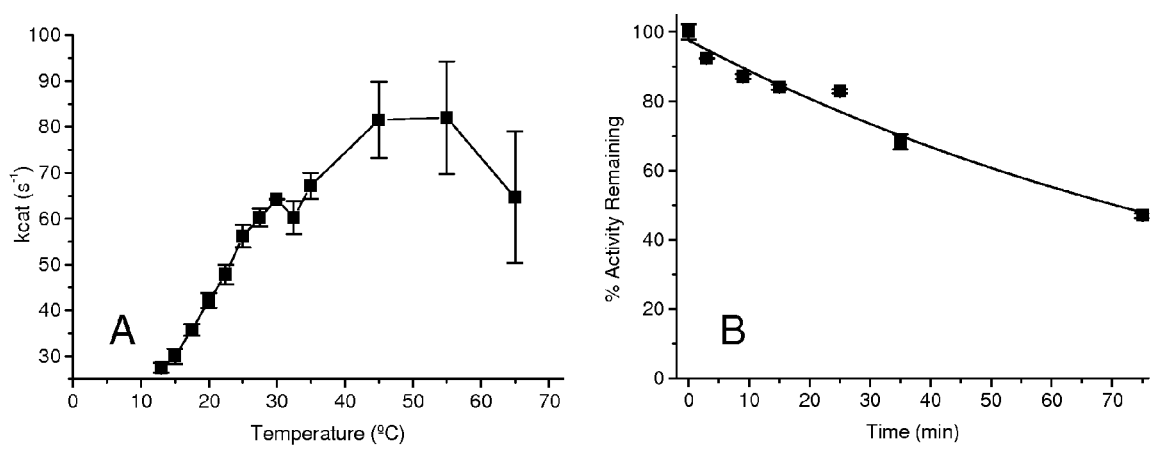
FIG. 8 illustrates (A) turnover rate dependence on temperature. XR was assayed in 500 mM xylose and 150 μM NADPH incubated at different temperature from 13 to 65° C. The optimal temperature of turnover was between 45 and 55° C.; (B) Thermal inactivation of XR at 40° C. A 27 ng/μl solution of XR was incubated in a heating block with a heated lid and aliquots were removed at various time points and assayed under saturating conditions. The inactivation at 40° C. was irreversible and followed first order kinetics with a half-life of 71 minutes.

Determination of thermal inactivation and rate dependence temperature. The dependence of the turnover rate on temperature was analyzed by measuring activity at a range of temperatures from 13° C. to 65° C. The activity measurements were converted into turnover number and plotted against temperature (FIG. 8A). The optimal temperature of turnover occurs between 45 and 55° C. At temperatures around 55° C. and higher, enzyme inactivation became significant in the 1 minute assay time. Therefore at temperatures above 55° C. the turnover number is lower. Data from 13 to 30° C. were used to determine the activation energy of the reaction. Non-linear least squares fitting of the Arrhenius equation resulted in an activation energy ($E_a$) of 37.3 kJ/mole for xylose reduction by ncXR.

While ncXR was stable at room temperature for at least 2 week and at 4° C. for months, at higher temperatures it was irreversibly inactivated. The rate of inactivation was further analyzed to determine the half-life of inactivation at 40° C. Residual XR activity was measured at various time points after incubation and plotted against time (FIG. 8B). The inactivation was determined to fit a first order exponential decay and the activity half-life was determined to be 71 minutes. Like many other $(\alpha/\beta)_8$ proteins, the natural thermostability for this mesophilic enzyme was high.

Example 10

Continuous production of xylitol. The effectiveness of the *Neurospora crassa* xylose reductase (XR) was demonstrated in a continuously operated enzyme membrane reactor (EMR) that also utilized a phosphite dehydrogenase mutant (PTDH). The PTDH used herein has a half-life at 50° C. that is 2.4-fold greater than the *Candida boidinii* formate dehydrogenase (FDH), an enzyme widely used for NADH regeneration. The optimum temperature of the 12x mutant is 57° C. and its half-life at 45° C. is 8440 minutes. The PTDH mutant had a 4-fold higher catalytic efficiency for NAD$^+$ and an 1000-fold higher efficiency for NADP$^+$ than the wild-type.

Figure 9:
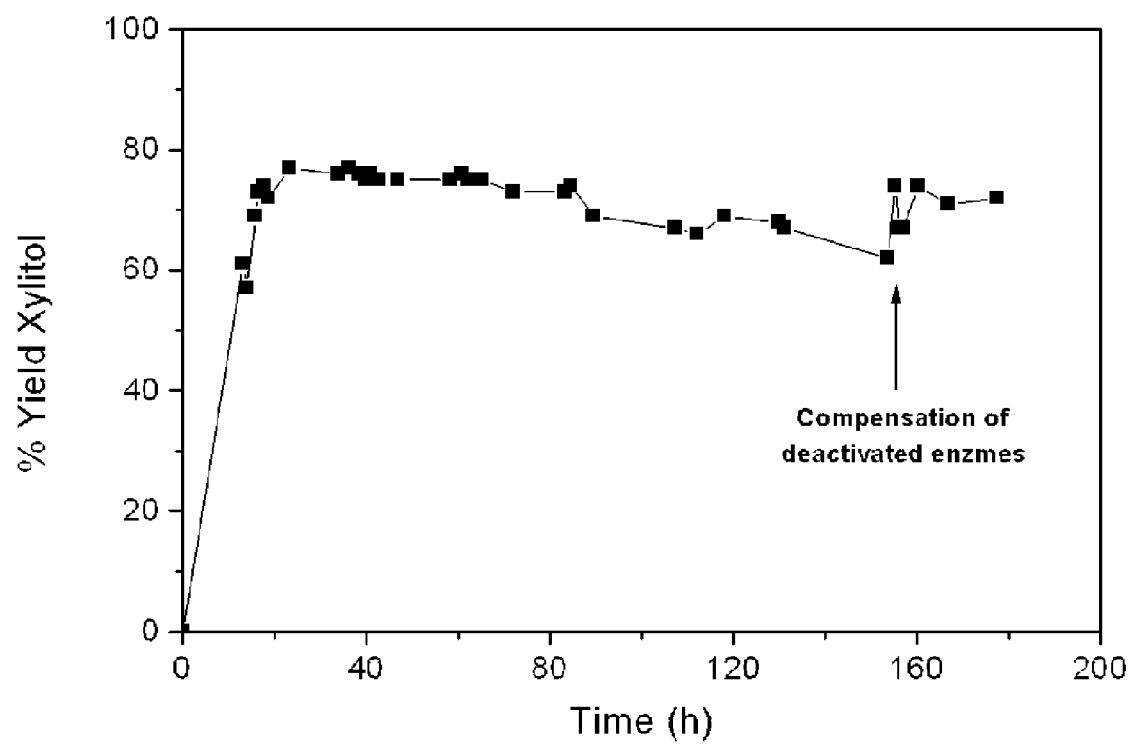
FIG. 9 shows the kinetics of a continuous production of xylitol in an enzyme membrane reactor using xylose reductase and the PTDH/phosphite regeneration system.

The conversion of D-xylose to xylitol was chosen as a model to evaluate the performance of xylose reductase in a PTDH/phosphite regeneration system. Several batch reactions were carried out to determine optimal reaction conditions for the reactor. Small-scale regeneration reactions carried out at an enzyme ratio of 3:2 (PTDH:XR), pH 6.9, 0.35 mM NADP$^+$, and a xylose to sodium phosphite ratio of 0.8 yielded the highest production of xylitol per hour. The continuous production of xylitol was performed in a 10-mL stainless-steel reactor. Table 4 shows the conditions and results for the continuous production of xylitol. The reactor was continuously operated for 180 hours and a substrate flow rate of 2.4 mL/h was used, resulting in a residence time of 4.2 hours. FIG. 9 shows the results for the production of xylitol in the EMR. In the absence of no side reaction in the system described here, yield and conversion are identical. The deactivation of the enzymes under these reactor conditions is approximately 2.8% per day. The conversion gradually decreased as time elapsed due to this deactivation. After 160 hours, 25% of both enzymes were injected into the reactor to compensate for enzyme deactivation and the conversion increased from 60% to 73%. An average space-time yield of 190 g L$^{-1}$ d$^{-1}$ was achieved during the 180 hours of operation. This indicates that the main reaction of xylitol production by xylose reductase was efficiently coupled to the enzymatic regeneration of the cofactor using the PTDH enzyme.

Any suitable reactor configuration and reaction conditions can be used to produce xylitol. Appropriate xylose containing medium and those that contain xylose precursors (e.g., xylan) can also be used.

Example 11

Production of ethanol. The xylose reductase, described herein can be used to produce ethanol from a xylose containing medium, such as, for example plant biomass. Xylose reductase can be provided in a purified form or can be provided as part of an expression system based on a heterologous host, such as, for example, recombinantly expressed xylose reductase in *E. coli* or *Saccharomyces cerevisiae* (yeast) or a plant cell. Plant biomass such as wood pulp, beet pulp can also be used.

Material and Methods

Materials. *Neurospora crassa* genomic sequence and XR protein sequences from xylose metabolizing yeast were accessed via the National Center for Biotechnology Information (NCBI, www.ncbi.nlm.nih.gov). *Neurospora crassa* 10333 were obtained from ATCC. *Escherichia coli* BL21 (DE3), vectors pET15b and pET26b, and Bugbuster HT™ were purchased from Novagen (Madison, Wis.). *E. coli* WM1788 were provided by Professor William Metcalf at the University of Illinois (Urbana, Ill.) (Haldimann et al., 2001). Cloned PfuTurbo DNA polymerase was obtained from Stratagene (La Jolla, Calif.), and Taq DNA polymerase was obtained from Promega (Madison, Wis.). Titan One Tube® RT-PCR kit and PCR grade dNTPs were obtained from Roche Applied Sciences (Indianapolis, Ind.). DNA-modifying enzymes DNase I, NdeI, DpnI, BamHI, and T4 DNA ligase and their corresponding buffers were purchased from New England Biolabs (NEB) (Beverly, Mass.). D-Glucose was purchased from Fisher Scientific (Pittsburgh, Pa.), while L-(+)-arabinose was purchased from Fluka (St. Louis, Mo.). D-Xylose, D-galactose, D-ribose, D-arabinose, ampicillin, kanamycin, isopropyl β-D-thiogalactopyranoside (IPTG), NADH, and NADPH were purchased from Sigma (St. Louis, Mo.). Other required salts and reagents were purchased from either Fisher (Pittsburgh, Pa.) or Sigma-Aldrich. The QIAprep spin plasmid mini-prep kit, QIAquick gel purification kit, RNeasy midiprep kit and QIAquick PCR purification kit were purchased from Qiagen (Valencia, Calif.). Various oligonucleotide primers were obtained from Integrated DNA Technologies (Coralville, Iowa). SDS-PAGE gel materials, electrophoresis equipment, protein size markers, size exclusion standards and Bio-Sil SEC-250, 300×7.8 mm column were purchased from Bio-Rad (Hercules, Calif.). $Co^{2+}$ Talon™ immobilized metal affinity resin was purchased from Clontech BD biosciences (San Jose, Calif.).

*N. Crassa* XR Gene Identification. BLAST searches based on protein sequence homology were performed on the website of the National Center for Biotechnology Information (www.ncbi.nlm.nih.gov)

Homology Modeling. The coordinates for xylose reductase from *Candida tenuis* (PDB accession code: 1MI3) and human aldose reductase (PDB accession code: 2ALR) were downloaded from the Protein Data Bank (www.pdb.org) database. Insight II software (Insight II, version 2000; Accelrys Inc., San Diego, Calif.) was used to structurally align these two structures to achieve the lowest root-mean-square (RMS) deviation between backbone atoms. The amino acid sequence of *N. crassa* XR was then aligned by pairwise alignment with this structural alignment, making sure that the aligned sequences represented homologous structural regions and fixing the alignment manually where necessary. Using default parameters with moderate refinement of the structure and loop regions the alignment was used as input for the automated MODELER module within Insight II. Nine structural models were created and the best model was selected on the basis of visual inspection for obvious flaws, the score from the Profiles3-D function, and the ProStat inspection of φ and ψ angles. NADPH was built using the coordinates of NADH in the *C. tenuis* crystal structure using molecule builder in Molecular Operating Environment (MOE; Chemical Computing Group Inc., Montreal, Canada). Hydrogen atoms were added to NADPH and the XR model and then NADPH was manually docked into the created model in MOE. Then the whole structure was subjected to energy minimization using the AMBER94 forcefield in MOE to relieve steric and torsional artifacts from the modeling and docking processes.

*N. crassa* RNA purification, Reverse Transcription-PCR, and Cloning. Rich potato media was prepared by boiling 200 g of cleaned potatoes in 1 l tap water for 1 hour. The solution was filtered through fine glass wool, 20 g glucose was added and the media was autoclaved. *N. crassa* were grown in 5 mL rich potato media at 30° C. for 24 hours with shaking at 250 rpm in the dark followed by induction with 150 mM xylose for 2 hours. The cells were harvested by centrifugation and washed with sterile water. Total RNA was purified from the cells using an RNeasy purification kit (Qiagen) following the manufacture's guidelines and treated with DNase I to remove residual genomic DNA. A reverse transcription polymerase chain reaction (RT-PCR) was performed using the Titan™ one tube system using the purified total RNA as a template following the manufactures guidelines. A control reaction consisted of the same protocol with the Titian™ enzyme mix heated to 95° C. for ten minutes to thermally inactivate the reverse transcriptase enzyme and removal of the reverse transcription thermocyler step. The primers used for the RT-PCR were: Forward 5'-GTA GCT ACG TCA CAT ATG GTT CCT GCT ATC AAG CTC-3' (SEQ ID NO:7) and Reverse 5'-CTG ATA GCG GAT CCC TAA CCG AAA ATC CAG AGG TTC TCA GCG GAG AAG TAG TTG-3' (SEQ ID NO: 8). The forward primer contained an NdeI restriction site shown in bold, while the reverse primer contained a BamHI restriction site shown in bold and overlapped an exon union site (underlined). The resulting RT-PCR product was isolated by agarose gel purification (Qiagen quick kit) and amplified by an additional 20 cycles of PCR. The product was digested with NdeI and BamHI restriction enzymes and purified again by agarose gel electrophoresis. The purified digested insert was ligated into both pET15b and pET26b vectors, which had been previously prepared by NdeI and BamHI digestion and gel purification. The ligation mixture was precipitated with n-butanol, resuspended in water, and used to transform *E. coli* WM1788 by electroporation. Positive clones were selected on Luria-Bertani (LB) solid media with ampicillin for pET15b and kanamycin for pET26b at 37° C. overnight. All colonies were then washed off the plates and grown to saturation in a 5 ml liquid LB culture from which the plasmids were purified (Qiagen plasmid miniprep) and used to transform *E. coli* BL21 (DE3) by heat shock. Positive clones were selected on LB solid media with the corresponding antibiotic, picked individually and assayed for XR activity by the cell lysate assay described herein. Frozen glycerol stocks of clones with XR activity were made and the plasmids were purified from the remaining culture. The XR genes from the selected clones and the RT-PCR product were sequenced in both directions with four overlapping reads at the Biotechnology Center of the University of Illinois using the BigDye® Terminator sequencing method and an ABI PRISM 3700 sequencer (Applied Biosystems, Foster City, Calif.).

Cell Lysate Activity of Heterologously Expressed XR. *E. coli* BL21 (DE3) harboring either the pET15b or pET26b derived vector were grown to saturation at 37° C. with shaking at 250 rpm. A small aliquot was used to inoculate a new culture, which was grown at 37° C. with shaking at 250 rpm until it reached $OD_{600}$ of ~0.6. At that time the cultures were induced with 0.5 mM IPTG and shaken at 25° C. and 250 rpm where protein expression was allowed to occur for 4 hr. Cell density was then normalized by $OD_{600}$ and 1 ml of cells were harvested by centrifugation and lysed by resuspension in 1 ml of 1 mg/ml lysozyme in 50 mM MOPS (pH 7.25). The cells were then frozen at −80° C. and thawed at room temperature. The lysate was then vortexed thoroughly and centrifuged to remove cell debris. Between 5 and 10 µl of the lysate was then used to start an assay as described herein in the Kinetic Analysis section with 250 mM xylose and 150 µM NADPH as the substrates.

Overexpression and Purification of XR. The buffers used for protein purification included start buffer A (SBA) (0.5 M NaCl, 20% glycerol, and 20 mM Tris-HCl, pH 7.6), start buffer B (SBB) (Start buffer A with 10 mM imidazole), and elution buffer (EB) (0.3 M imidazole, 0.5 M NaCl, 20% glycerol, and 20 mM Tris-HCl, pH 7.6). The E. coli BL21 (DE3) transformants with pET15b-derived vectors were grown in LB medium containing 100 μg/ml ampicillin at 37° C. with good aeration (shaking at 250 rpm). When the log phase was reached ($OD_{600}$~0.6), cells were induced with IPTG (final concentration 0.3 mM) and incubated at 25° C. with shaking at 250 rpm for 8 h. Cells were harvested by centrifugation at 5000×g, 4° C., for 15 min, then resuspended in 10 ml/g (cell pellet) SBA containing 1 mg/ml of lysozyme, and stored at −80° C. The frozen cell suspension was thawed at room temperature and lysed by sonication using a Fisher Sonic Dismembrator 500 (Pittsburgh, Pa.) with amplitude set at 40% and with a pulse sequence of 5 s on and 9.9 s off, for ~10 min. Cells were centrifuged at 20000×g at 4° C. for 10 min, and the supernatant containing the crude extract was filtered through a 0.22 μm filter to remove any particles. The clarified supernatant was purified by FPLC, with a flow rate of 5 ml/min and fraction size of 5 mL. The Bio-Rad BioLogic LP FPLC system was fitted with a column packed with 10 ml Talon™ resin, which was charged and equilibrated according to the manufacturer's protocol. The clarified supernatant (from ~5 g of cell paste) was loaded through the pump and washed with 100 ml SBA. This was followed by washing the column with 50 ml of SBB and elution with a linear gradient into 100% EB in 10 min and finished by a wash with 50 ml of EB. The elution fractions were monitored at 280 nm. The XR-containing fractions were concentrated and desalted using a Millipore Amicon 8400 stirred ultrafiltration cell with a YM10 membrane at 4° C., washed three times with 75 ml of 50 mM MOPS buffer (pH 7.25). The enzyme was then stored in 10% glycerol in small aliquots at −80° C. The $His_6$-tag (SEQ ID NO: 1) could be removed by incubation with thrombin overnight at 4° C. leaving three residues (GlySerHis) attached to the N-terminus of the protein.

Protein Characterization. Protein concentration was determined by the Bradford method (1996) using bovine serum albumin as a standard. Additionally, the protein concentration was determined with similar results using the extinction coefficient of 56 $mM^{-1}$ at 280 nm estimated using Biology Workbench (http://workbench.sdsc.edu/). The purity of the protein was analyzed by SDS-PAGE stained with Coomassie brilliant blue. To determine the quaternary structure, size exclusion HPLC was preformed. An Agilent 1100 series solvent selector, pump, column, and detector modules were coupled a Bio-Sil SEC-250, 300×7.8 mm column with a mobile phase of 0.1 M $NaPO_3$, 0.15 M NaCl, 0.01 M $NaN_3$, pH 6.8. A Bio-Rad standard (cat. 151-1901) was used to standardize the column at a flow rate of 1 ml/min with the detector set at 280 nm. 20 μl samples were prepared by diluting the purified enzyme or the purified enzyme in 15% SDS 10-fold in the mobile phase. The standard curve was created by plotting the molecular mass against retention time and solving the log function by non-linear regression using Origin 5.0 (Microcal Software Inc.). The purified protein was also subjected to mass analysis by ESI-Q-TOF mass spectrometry at the Mass Spectrometry Laboratory at University of Illinois.

Kinetic Analysis. Initial rates were determined by monitoring the decrease in absorbance at 340 nm, corresponding to the consumption of NAD(P)H ($\epsilon_{NAD(P)H}$=6.22 $mM^{-1}$ $cm^{-1}$). All initial rate assays were carried out at 25° C. in 50 mM MOPS pH 6.3 using a Varian Cary 100 Bio UV-visible spectrophotometer unless otherwise noted. The reaction was initiated by addition of 0.1-1 μg of XR. Concentrations of NAD (P)H stock solutions were determined by UV-visible spectroscopy. Michaelis-Menten constants $V_{max}$ and $K_M$ were determined by a series of assays where the concentration of one substrate was varied while the second substrate was kept at saturating concentration (at least 5-fold greater than the corresponding $K_M$). The data were then converted to turnover number and fitted by non-linear regression analysis to the Michaelis-Menten equation using Origin 5.0. For various sugar substrates, NADPH concentrations were held at 150-200 μM. For determination of $K_{M,NADPH}$, a 5 cm path length cuvette was utilized to minimize errors. All assays were performed in duplicate or triplicate at least two times. The kinetic data presented represent averages of statistically relevant measurements and with their associated standard deviations.

Optimal Temperature and Thermal Inactivation. Thermal inactivation was determined by incubating XR in a heating block with a heated lid at 40° C. in 50 mM MOPS (pH 6.3) at a protein concentration of 27 ng/μL. Aliquots of 30 μL were removed at various times and placed on ice. The samples were then assayed in triplicate with saturating concentrations of xylose and NADPH in triplicate. Initial activity was measured as described in the Kinetic Analysis section at each time point starting the reaction with 0.27 μg of XR per assay. The data were plotted as the residual activity versus the incubation time and then analyzed by exponential curve fitting to determine the half-life of thermal inactivation, which followed first-order kinetics. The optimal temperature of turnover was determined by incubating 500 mM xylose and 150 μM NADPH at various temperatures from 13° C. to 65° C. The assay was started by the addition of 0.5 μg of XR while a recirculating water bath with temperature controlled cuvette holder was used to maintain the temperature during the assay. To determine the activation energy the data was fitted to the Arrhenius equation where k is the rate, A is a constant, $E_a$ is the activation energy, R is the ideal gas constant (8.314×$10^{-3}$ kJ/mol K), and T is the temperature in Kelvin.

$$k=Ae^{(-Ea/RT)}$$ (Arrhenius Equation)

pH rate profile. A universal buffer consisting of 25 mM MES, 25 mM TRIS, and 50 mM acetate was utilized to cover the entire pH range. 1 M xylose and 200 μM NADPH were prepared at various pH values from 4.0 to 8.0. The $K_M$ values at the pH extremes were checked to verify that substrate concentrations remained saturating. Assays were started by the addition of 1 μg of XR and initial activity was measured as described in the Kinetic Analysis section at each pH.

TABLE 1

Parameters for N. Crassa Xylose Reductase[a]

| Coenzyme | $K_M$ NAD(P)H (μM) | $k_{cat}$ ($min^{-1}$) | $k_{cat}$/$K_{M, NAD(P)H}$ ($μM^{-1} min^{-1}$) | $K_M$ Xylose (mM) |
|---|---|---|---|---|
| NADPH | 1.8 ± 0.5 | 3600 ± 100 | 2000 | 34 ± 4 |
| NADH | 16 ± 4 | 310 ± 10 | 19 | 37 ± 7 |

[a]All assays were performed at 25° C. in 50 mM MOPS pH 6.3

TABLE 2

Parameters for N. Crassa Xylose Reductase with Other Substrates[a]

| Substrate | $k_{cat}$ (min$^{-1}$) | $k_M$ (mM) | $k_{cat}/K_M$ (mM$^{-1}$min$^{-1}$) | Percent Efficiency |
|---|---|---|---|---|
| D-Xylose | 3600 ± 200 | 34 ± 4 | 110 | 100% |
| D-Ribose | 3120 ± 100 | 70 ± 10 | 45 | 41% |
| L-Arabinose | 1800 ± 100 | 40 ± 10 | 45 | 41% |
| D-Galactose | 1800 ± 100 | 180 ± 30 | 10 | 9.1% |
| D-Glucose | 1320 ± 100 | 360 ± 60 | 3.60 | 3.3% |

[a]All assays were performed at 25° C. in 50 mM MOPS pH 6.3

TABLE 3

Properties of Xylose Reductases from Various Organisms

| Organism (reference) | MW Subunit (kDa) | MW Native (kDa) | $k_{cat}$ (min$^{-1}$)[a] | $K_{M, Xylose}$ (mM)[a] | $k_{cat}/K_{M, Xylose}$ (mM$^{-1}$min$^{-1}$)[a] | $K_{M, NADPH}$ (πM) | $k_{cat}/K_{M, NADPH}$ (πM$^{-1}$min$^{-1}$) | $K_{M, NADH}$ (πM) | Optimal pH |
|---|---|---|---|---|---|---|---|---|---|
| N. crassa (this work) | 38.4 | 53 | 3600 | 34 | 106 | 1.8 | 2000 | 16 | 5.5 |
| C. Intermedia (31, 34) | 36 | 58 | 900 | 50 | 18 | 56 | 16 | 28 | 6.0 |
| C. parapsilosis (30) | 36.6 | 69 | 3100[b] | 32[b] | 98[b] | 37 | 84[b] | 3.3 | 6.0 |
| C. tropicalis (43) | 36.5 | 58 | ND[c] | 30-37 | ND[c] | 9-18 | ND[c] | ND[c] | 6.0 |
| C. tenuis (13, 33) | 36 | 60 | 1300 | 72 | 18 | 4.8 | 271 | 25 | 6.0 |
| P. tannophilus (9) | 38 | 38 | 600 | 162 | 4 | 59 | 10 | ND[c] | 7.0 |
| P. stipitus (41) | 34 | 65 | 1500 | 42 | 36 | 9 | 167 | 21 | 6.0 |
| S. cerevisiae (18) | 33 | 33 | 860 | 13.6 | 63 | 7.6 | 113 | ND[c] | ND[c] |

[a]with NADPH as cofactor except for C. parapsilosis
[b]with NADH as cofactor
[c]Not Determined

TABLE 4

Conditions and results for the continuous production of xylitol in an enzyme membrane reactor.

Feed Concentrations

| | |
|---|---|
| Xylose | 300 mM |
| Sodium phosphite | 375 mM |
| NADP$^+$ | 0.35 mM |
| Sodium azide | 0.025% (w/v) |

Reactor Conditions

| | |
|---|---|
| XR | 2.0 mg mL$^{-1}$ |
| PTDH | 3.0 mg mL$^{-1}$ |
| BSA | 1.0 mg mL$^{-1}$ |
| Reactor volume | 10 mL |
| pH | 6.9 |
| Temperature | 25° C. |
| Residence time | 4.2 h |
| Mean conversion | 72% |
| Space-time yield | 190 g L$^{-1}$ d$^{-1}$ |
| Total turnover number | 617 |
| Enzyme deactivation | 2.8% d$^{-1}$ |

DOCUMENTS

The following documents are incorporated by reference to the extent they relate to or describe materials or methods disclosed herein.

Amore et al., 1991. Gene 109:89-97.
Aspinall, G. O. 1980. Academic Press, New York.
Bedford et al., 1987. J Biol Chem 262:14255-9.
Bohren et al., 1994. Biochemistry 33:2021-2032.
Bolen et al., 1985. Biotechnology and Bioengineering 27:302-307.
Bradford, M. M. 1976. Anal Biochem 72:248-54.
Bruinenberg et al., 1984. Appl Environ Microbiol 19:256-260.
Deshpande et al., 1986. Enzyme and Microbial Technology 8:149-152.
Ditzelmuller et al., 1984. Canadian Journal of Microbiology 30:1330-1336.
Galagan et al., 2003. Nature 422:859-868.
Grimshaw, C. E. 1992. Biochemistry 31:10139-45.
Gulbis et al., 1999. Cell 97:943-52.
Hacker et al., 1999. Biol Chem 380:1395-403.
Hahn-Hagerdal et al., 2001. Adv Biochem Eng Biotechnol 73:53-84.
Haldimann, A., and B. L. Wanner. 2001. J Bacteriol 183: 6384-93.
Ho et al., 1990. Enzyme Microb Technol 12:33-9.
Ikemi et al., 1990. Biotechnology and Bioengineering 36:149-154.
Jeong et al., 2002. Fems Microbiology Letters 209:223-228.
Jeong et al., 2001. Yeast 18:1081-1089.
Jez et al., 2001. Chem Biol Interact 130-132:499-525.
Jin et al., 2002. Applied and Environmental Microbiology 68:1232-1239.
Kador et al., 1985. Annu Rev Pharmacol Toxicol 25:691-714.
Kang et al., 2003. Appl Biochem Biotechnol 105-108:265-76.
Kavanagh et al., 2002. Biochemistry 41:8785-95.
Klimacek et al., 2001. FEBS Lett 500:149-52.
Klimacek et al., 2003. Chem Biol Interact 143-144:523-32.
Kozma et al., 2002. J Biol Chem 277:16285-93.
Kuhn et al., 1995. Appl Environ Microbiol 61:1580-5.
Laemmli, U. K. 1970. Nature 227:680-5.
Lee et al., 2003. Appl Environ Microbiol 69:6179-88.
Mayr et al., 2000. J Chromatogr B Biomed Sci Appl 737:195-202.
Mishra et al., 1984. Applied and Environmental Microbiology 48:224-228.
Neuhauser et al., 1997. Biochem J 326 (Pt 3):683-92.
Nidetzky et al., 2003. J Agric Food Chem 51:7930-5.
Nidetzky et al., 1996. Biotechnology and Bioengineering 52:387-396.
Nidetzky et al., 1998. Ann N Y Acad Sci 864:442-5.
Rao et al., 1983. Enzyme and Microbial Technology 5:133-136.
Rawat et al., 1993. Biotechnology Letters 15:1173-1178.
Rawat et al., 1996. Biochim Biophys Acta 1293:222-30.

Richard et al., 2000. Fems Microbiology Letters 190:39-43.
Verduyn et al., 1985. Biochemical Journal 226:669-677.
Wilson et al., 1992. Science 257:81-84.
Yokoyama et al., 1995. Journal of Fermentation and Bioengineering 79:217-223.
U.S. Pat. No. 6,582,944

We claim:

1. A method of producing xylitol, the method comprising:
   (a) obtaining a highly active form of xylose reductase comprising the amino acid sequence of a *Neurospora crassa* xylose reductase as in SEQ ID NO: 2; and
   (b) providing conditions to produce xylitol from a xylose containing medium.

2. The method of claim 1 further comprising use of a phosphite dehydrogenase (PTDH) for co-factor regeneration.

3. The method of claim 1, wherein the production of xylitol is in a membrane reactor.

4. The method of claim 3, wherein the production of xylitol in the membrane reactor is continuous.

5. The method of claim 1, wherein the production of sugar alcohol utilizes a phosphite dehydrogenase-based NADP regeneration system.

6. A method of producing a sugar alcohol, the method comprising:
   (a) obtaining a highly active form of xylose reductase comprising the amino acid sequence of a *Neurospora crassa* xylose reductase as in SEQ ID NO: 2; and
   (b) providing conditions to produce sugar alcohol from a xylose containing medium.

7. The method of claim 6 wherein the sugar alcohol is sorbitol.

* * * * *

UNITED STATES PATENT AND TRADEMARK OFFICE
CERTIFICATE OF CORRECTION

PATENT NO. : 7,592,163 B2   Page 1 of 2
APPLICATION NO. : 12/123279
DATED : September 22, 2009
INVENTOR(S) : Zhao et al.

It is certified that error appears in the above-identified patent and that said Letters Patent is hereby corrected as shown below:

On the title page item (57), the Abstract should read as follows:

--A new xylose reductase encoding gene from *Neurospora crassa* was heterologously expressed in *E. coli* as a His-tag fusion protein and subsequently purified in high yield. This xylose reductase was shown to have a high turnover rate and catalytic efficiency, high stability at room temperature, broad pH profile, and a preference of NADPH over NADH. This enzyme is utilized in production of xylitol and other sugar alcohols such as sorbitol and also in the metabolic enhancement of organisms used for fermentation of plant biomass into ethanol.--

Column 2, line 36 should read as follows:
--biomass to ethanol because it produces cellulase and xylanase--

Column 3, line 15 should read as follows:
--xylose reductase further includes the following characteristics:--

Column 4, line 42 should read as follows:
--Turnover number ($k_{cat}$)--

Column 5, line 31 should read as follows:
--(SEQ ID NO: 1). Lanes 3 and 5 contain the respective soluble--

Signed and Sealed this

First Day of June, 2010

David J. Kappos
*Director of the United States Patent and Trademark Office*

Column 11, line 65 should read as follows:

--weeks and at 4 °C for months, at higher temperatures it was--

Column 12, line 19 should read as follows:

--4-fold higher catalytic efficiency for $NAD^+$ and a 1000-fold--